(12) United States Patent
Fanslow, III et al.

(10) Patent No.: US 7,449,555 B2
(45) Date of Patent: Nov. 11, 2008

(54) ANTIBODIES OF ANGIOGENESIS INHIBITING DOMAINS CD148

(75) Inventors: William C. Fanslow, III, Normandy Park, WA (US); Revital Kariv, Bellevue, WA (US); James F. Smothers, Lake Forest Park, WA (US)

(73) Assignee: Amgen Inc., Thousand Oaks, CA (US)

( * ) Notice: Subject to any disclaimer, the term of this patent is extended or adjusted under 35 U.S.C. 154(b) by 194 days.

(21) Appl. No.: 11/112,304

(22) Filed: Apr. 22, 2005

(65) Prior Publication Data

US 2006/0002931 A1    Jan. 5, 2006

Related U.S. Application Data

(60) Provisional application No. 60/564,885, filed on Apr. 23, 2004, provisional application No. 60/565,158, filed on Apr. 23, 2004, provisional application No. 60/571,566, filed on May 14, 2004, provisional application No. 60/585,686, filed on Jul. 6, 2004.

(51) Int. Cl.
*C07K 16/00*    (2006.01)
*A61K 39/40*    (2006.01)

(52) U.S. Cl. .................. 530/388.1; 424/141.1

(58) Field of Classification Search ........... None
See application file for complete search history.

(56) References Cited

U.S. PATENT DOCUMENTS

| 7,176,289 B1 * | 2/2007 | Daniel et al. ............. 530/388.1 |
| 7,205,121 B2 * | 4/2007 | Palka-Hamblin et al. ...... 435/21 |
| 2003/0215899 A1 | 11/2003 | Meng et al. ................... 435/21 |
| 2004/0161821 A1 | 8/2004 | Palka-Hamblin et al. ... 435/69.1 |
| 2005/0272054 A1 | 12/2005 | Cargill et al. .................. 435/6 |
| 2005/0287140 A1 * | 12/2005 | Smothers et al. ......... 424/144.1 |

FOREIGN PATENT DOCUMENTS

WO    WO 2005/117970    12/2005

OTHER PUBLICATIONS

International Search Report for International Application No. PCT/US2005/014084 (Feb. 26, 2007).

* cited by examiner

*Primary Examiner*—Michail A Belyavskyi
(74) *Attorney, Agent, or Firm*—David B. Ran; Christopher L. Wight; Brinks Hofer Gilson & Lione

(57) ABSTRACT

Anti-CD148 antibodies and antigen-binding regions thereof, as well as pharmaceutical compositions comprising such antibodies and antigen-binding regions, are described. Also described are methods of using such antibodies and antigen-binding regions to bind CD148 epitopes and activate CD148 function, such as inhibition of angiogenesis. Epitopes that can be used to activate CD148 function and anti-angiogenesis activity are also described, as well as methods of identifying compounds that can bind them.

19 Claims, 16 Drawing Sheets

Figure 1A
Ab-1 VH Domain

```
              10         20         30         40         50         60
         ----------|----------|----------|----------|----------|----------|
Query  : GAGGTGCAGCTGTTGGAGTCTGGGGGAGGCTTGGTACAGCCTGGGGGGTCCCTGAGACTC
Frame1 : E   V   Q   L   L   E   S   G   G   G   L   V   Q   P   G   G   S   L   R   L 70         80         90        100        110        120
         ----------|----------|----------|----------|----------|----------|
Query  : TCCTGTGCAGCCTCTGGATTCACCTTTAGCAGCTATGCCATGAGCTGGGTCCGCCAGGCT
Frame1 : S   C   A   A   S   G   F   T   F   S   S   Y   A   M   S   W   V   R   Q   A 20        130        140        150        160        170        180
         ----------|----------|----------|----------|----------|----------|
Query  : CCAGGGAAGGGGCTGGAGTGGGTCTCAGCTATTAGTGGTAGTGGTGGTAGCACATACTAC
Frame1 : P   G   K   G   L   E   W   V   S   A   I   S   G   S   G   G   S   T   Y   Y 80        190        200        210        220        230        240
         ----------|----------|----------|----------|----------|----------|
Query  : GCAGACTCCGTGAAGGGCCGGTTCACCATCTCCAGAGACAATTCCAAGAACACGCTGTAT
Frame1 : A   D   S   V   K   G   R   F   T   I   S   R   D   N   S   K   N   T   L   Y 40        250        260        270        280        290        300
         ----------|----------|----------|----------|----------|----------|
Query  : CTGCAAATGAACAGCCTGAGAGCCGAGGACACGGCCGTGTATTACTGTGCGAGAGGTCGG
Frame1 : L   Q   M   N   S   L   R   A   E   D   T   A   V   Y   Y   C   A   R   G   R 310        320        330        340        350        360
         ----------|----------|----------|----------|----------|----------|
Query  : ACTGAGGTGGCAACCCCGGCGGCGCCTACTGGGGCCAAGGGACAATGGTCACCGTCTCGAGT
Frame1 : T   E   V   A   T   P   G   A   Y   W   G   Q   G   T   M   V   T   V   S   S
```

Figure 1B
Ab-1 VL Domain

```
              10         20         30         40         50         60
     ----------|----------|----------|----------|----------|----------|
Query  : CAGGCTGTGCTGACTCAGCCGTCCTCAGTGTCTGGGGCCCCAGGGCAGAGGGTCACCATC
Frame1 : Q   A   V   L   T   Q   P   S   S   V   S   G   A   P   G   Q   R   V   T   I 70         80         90        100        110        120
     ----------|----------|----------|----------|----------|----------|
Query  : TCCTGCACTGGGAGCAGCTCCAACATCGGGGCAGGTTATGATGTACACTGGTACCAGCAG
Frame1 : S   C   T   G   S   S   S   N   I   G   A   G   Y   D   V   H   W   Y   Q   Q 20        130        140        150        160        170        180
     ----------|----------|----------|----------|----------|----------|
Query  : CTTCCAGGAACAGCCCCCAAACTCCTCATCTATGGTAACAGCAATCGGCCCTCAGGGGTC
Frame1 : L   P   G   T   A   P   K   L   L   I   Y   G   N   S   N   R   P   S   G   V 80        190        200        210        220        230        240
     ----------|----------|----------|----------|----------|----------|
Query  : CCTGACCGATTCTCTGGCTCCAAGTCTGGCACCTCAGCCTCCCTGGCCGTCACTGGGCTC
Frame1 : P   D   R   F   S   G   S   K   S   G   T   S   A   S   L   A   V   T   G   L 40        250        260        270        280        290        300
     ----------|----------|----------|----------|----------|----------|
Query  : CAGGCTGAGGATGAGGCTGATTATTACTGCCAGTCCTATGACAGCAGCCTGAGTGATGTG
Frame1 : Q   A   E   D   E   A   D   Y   Y   C   Q   S   Y   D   S   S   L   S   D   V 310        320        330
     ----------|----------|----------|--- 333
Query  : GTATTCGGCGGAGGGACCAAGCTGACCGTCCTA
Frame1 : V   F   G   G   G   T   K   L   T   V   L
```

Figure 2A
Ab-2 VH Domain

```
                 10         20         30         40         50         60
            ----------|----------|----------|----------|----------|----------|
Query   : GAGGTGCAGCTGTTGGAGTCTGGGGGAGGCTTGGTACAGCCTGGGGGGTCCCTGAGACTC
Frame1  : E  V  Q  L  L  E  S  G  G  G  L  V  Q  P  G  G  S  L  R  L 70         80         90        100        110        120
            ----------|----------|----------|----------|----------|----------|
Query   : TCCTGTGCAGCCTCTGGATTCACCTTTAGCAGCTATGCCATGAGCTGGGTCCGCCAGGCT
Frame1  : S  C  A  A  S  G  F  T  F  S  S  Y  A  M  S  W  V  R  Q  A 20        130        140        150        160        170        180
            ----------|----------|----------|----------|----------|----------|
Query   : CCAGGGAAGGGGCTGGAGTGGGTCTCAGCTATTAGTGGTAGTGGTGGTAGCACATACTAC
Frame1  : P  G  K  G  L  E  W  V  S  A  I  S  G  S  G  G  S  T  Y  Y 80        190        200        210        220        230        240
            ----------|----------|----------|----------|----------|----------|
Query   : GCAGACTCCGTGAAGGGCCGGTTCACCATCTCCAGAGACAATTCCAAGAACACGCTGTAT
Frame1  : A  D  S  V  K  G  R  F  T  I  S  R  D  N  S  K  N  T  L  Y 40        250        260        270        280        290        300
            ----------|----------|----------|----------|----------|----------|
Query   : CTGCAAATGAACAGCCTGAGAGCCGAGGACACGGCCGTGTATTACTGTGCGAGATATCGG
Frame1  : L  Q  M  N  S  L  R  A  E  D  T  A  V  Y  Y  C  A  R  Y  R 310        320        330        340        350        360
            ----------|----------|----------|----------|----------|----------|
Query   : GACTATGGTGGTAACTCCCACCTCTTTGACTACTGGGGGCAAGGGACCACGGTCACCGTC
Frame1  : D  Y  G  G  N  S  H  L  F  D  Y  W  G  Q  G  T  T  V  T  V 60
            ------ 366
Query   : TCGAGT
Frame1  : S  S
```

Figure 2B
Ab-2 VL Domain

```
              10        20        30        40        50        60
              |---------|---------|---------|---------|---------|---------|
Query    : GAAATTGTGATGACGCAGTCTCCGTCCTCCCTGCCTGCCTCTGTAGGAGACAGAGTCACC
Frame1   : E  I  V  M  T  Q  S  P  S  S  L  P  A  S  V  G  D  R  V  T 70        80        90       100       110       120
              |---------|---------|---------|---------|---------|---------|
Query    : ATCACTTGTCGGGCAAGTCAGAACATTAAGACCTATTTGCACTGGTACCAACAGAAGCCA
Frame1   : I  T  C  R  A  S  Q  N  I  K  T  Y  L  H  W  Y  Q  Q  K  P 20       130       140       150       160       170       180
              |---------|---------|---------|---------|---------|---------|
Query    : GGGAAAGCCCCTAACCTCCTGATCTATGCTGCATCCAATTTGCAAAATGGGGTCCCATCA
Frame1   : G  K  A  P  N  L  L  I  Y  A  A  S  N  L  Q  N  G  V  P  S 80       190       200       210       220       230       240
              |---------|---------|---------|---------|---------|---------|
Query    : AGGTTCAGTGGCAGTGGATCTGGGACAGATTTTACTCTCACCATCAGCAGTCTGCAACCT
Frame1   : R  F  S  G  S  G  S  G  T  D  F  T  L  T  I  S  S  L  Q  P 40       250       260       270       280       290       300
              |---------|---------|---------|---------|---------|---------|
Query    : GAAGATTTTGCTACTTACTTCTGTCAACAGAGTTACATTACCCCTCCCACGTTCGGCCAA
Frame1   : E  D  F  A  T  Y  F  C  Q  Q  S  Y  I  T  P  P  T  F  G  Q 310       320
              |---------|---------|- 321
Query    : GGGACACGACTGGAGATTAAA
Frame1   : G  T  R  L  E  I  K
```

Figure 3A
Ab-3 VH Domain

```
              10         20         30         40         50         60
         ----------|----------|----------|----------|----------|----------|
Query  : GGGGTCCAGCTGGTACAGTCTGGGGCTGAGGTGAAGAAGCCTGGGGCCTCAGTGAAGGTT
Frame1 : G  V  Q  L  V  Q  S  G  A  E  V  K  K  P  G  A  S  V  K  V 70         80         90        100        110        120
         ----------|----------|----------|----------|----------|----------|
Query  : TCCTGCAAGGCATCTGGATACACCTTCACCAGCTACTATATGCACTGGGTGCGACAGGCC
Frame1 : S  C  K  A  S  G  Y  T  F  T  S  Y  Y  M  H  W  V  R  Q  A 20        130        140        150        160        170        180
         ----------|----------|----------|----------|----------|----------|----------|
Query  : CCTGGACAAGGGCTTGAGTGGATGGGAATAATCAACCCTAGTGGTGGTAGCACAAGCTAC
Frame1 : P  G  Q  G  L  E  W  M  G  I  I  N  P  S  G  G  S  T  S  Y 80        190        200        210        220        230        240
         ----------|----------|----------|----------|----------|----------|----------|
Query  : GCACAGAAGTTCCAGGGCAGAGTCACCATGACCAGGGACACGTCCACGAGCACAGTCTAC
Frame1 : A  Q  K  F  Q  G  R  V  T  M  T  R  D  T  S  T  S  T  V  Y 40        250        260        270        280        290        300
         ----------|----------|----------|----------|----------|----------|----------|
Query  : ATGGAGCTGAGCAGCCTGAGATCTGAGGACACGGCCGTATATTACTGTGCTAGAAGGGTT
Frame1 : M  E  L  S  S  L  R  S  E  D  T  A  V  Y  Y  C  A  R  R  V 310        320        330        340        350
         ----------|----------|----------|----------|----------|---- 354
Query  : ATTCGGGTGCTTTTGATATCTGGGGCCAGGGGACAATGGTCACCGTCTCGAGT
Frame1 : S  G  A  F  D  I  W  G  Q  G  T  M  V  T  V  S  S
```

Figure 3B
Ab-3 VL Domain

```
                  10        20        30        40        50        60
          ----------|---------|---------|---------|---------|---------|
Query   : GACATCCAGATGACCCAGTCTCCTTCCACCCTGTCTGCATCTATTGGAGACAGAGTCACC
Frame1  : D   I   Q   M   T   Q   S   P   S   T   L   S   A   S   I   G   D   R   V   T 70        80        90       100       110       120
          ----------|---------|---------|---------|---------|---------|
Query   : ATCACCTGCCGGGCCAGTGAGGGTATTTATCACTGGTTGGCCTGGTATCAGCAGAAGCCA
Frame1  : I   T   C   R   A   S   E   G   I   Y   H   W   L   A   W   Y   Q   Q   K   P 20       130       140       150       160       170       180
          ----------|---------|---------|---------|---------|---------|
Query   : GGGAAAGCCCCTAAACTCCTGATCTATAAGGCCTCTAGTTTAGCCAGTGGGGCCCCATCA
Frame1  : G   K   A   P   K   L   L   I   Y   K   A   S   S   L   A   S   G   A   P   S 80       190       200       210       220       230       240
          ----------|---------|---------|---------|---------|---------|
Query   : AGGTTCAGCGGCAGTGGGTCTGGGACAGATTTCACTCTCACCATCAGCAGCCTGCAGCCT
Frame1  : R   F   S   G   S   G   S   G   T   D   F   T   L   T   I   S   S   L   Q   P 40       250       260       270       280       290       300
          ----------|---------|---------|---------|---------|---------|
Query   : GATGATTTTGCAACTTATTACTGCCAACAATATAGTAATTATCCGCTCACTTTCGGCGGA
Frame1  : D   D   F   A   T   Y   Y   C   Q   Q   Y   S   N   Y   P   L   T   F   G   G 310       320
          ----------|---------|- 321
Query   : GGGACCAAGCTGGAGATCAAA
Frame1  : G   T   K   L   E   I   K
```

Figure 4A
Ab-4 VH Domain

```
                10         20         30         40         50         60
            ----------|----------|----------|----------|----------|----------|
Query   : CAGGTGCAGCTGGTGCAGTCTGGGGCTGAGGTGAAGAAGCCTGGGGCCTCAGTGAAGGTT
Frame1  : Q   V   Q   L   V   Q   S   G   A   E   V   K   K   P   G   A   S   V   K   V 70         80         90         100        110        120
            ----------|----------|----------|----------|----------|----------|
Query   : TCCTGCAAGGCATCTGGATACACCTTCACCAGCTACTATATGCACTGGGTGCGACAGGCC
Frame1  : S   C   K   A   S   G   Y   T   F   T   S   Y   Y   M   H   W   V   R   Q   A 20        130        140        150        160        170        180
            ----------|----------|----------|----------|----------|----------|
Query   : CCTGGACAGGGGCTTGAGTGGATGGGGATAATCAACCCTAGTGATGGTAGCACAAGGTAC
Frame1  : P   G   Q   G   L   E   W   M   G   I   I   N   P   S   D   G   S   T   R   Y 80        190        200        210        220        230        240
            ----------|----------|----------|----------|----------|----------|
Query   : GTAGAGAAGTTCCAGGGCAGAGTCACCATGACCAGGGACACGTCCACGAGCACAGTCTAC
Frame1  : V   E   K   F   Q   G   R   V   T   M   T   R   D   T   S   T   S   T   V   Y 40        250        260        270        280        290        300
            ----------|----------|----------|----------|----------|----------|
Query   : ATGGAGTTGAGCAGCCTGAGATCTGAGGACACGGCCGTGTATTTCTGTGCGAGAGGCATG
Frame1  : M   E   L   S   S   L   R   S   E   D   T   A   V   Y   F   C   A   R   G   M 310        320        330        340        350        360
            ----------|----------|----------|----------|----------|----------|
Query   : GGACCCGGCCCCCACTACCACTTCTACATGGACGTGTGGGGCAAAGGGACAATGGTCACC
Frame1  : G   P   G   P   H   Y   H   F   Y   M   D   V   W   G   K   G   T   M   V   T 60
            ---------- 369
Query   : GTCTCCTCA
Frame1  : V   S   S
```

Figure 4B
Ab-4 VL Domain

```
               10         20         30         40         50         60
         ----------|----------|----------|----------|----------|----------|
Query  : TCGTCTGAGCTGACTCAGGACCCTGCTGTGTCTGTGGCCTTGGGACAGACAGTCAGGATC
Frame1 : S   S   E   L   T   Q   D   P   A   V   S   V   A   L   G   Q   T   V   R   I 70         80         90        100        110        120
         ----------|----------|----------|----------|----------|----------|
Query  : ACTTGCCAAGGAGACAGTCTCAGAAGCTATTACACAAACTGGTTCCAGCAGAAGCCAGGA
Frame1 : T   C   Q   G   D   S   L   R   S   Y   Y   T   N   W   F   Q   Q   K   P   G 20         130        140        150        160        170        180
         ----------|----------|----------|----------|----------|----------|
Query  : CAGGCCCCTCTACTTGTCGTCTATGCTAAAAATAAGCGGCCCTCAGGGATCCCAGACCGA
Frame1 : Q   A   P   L   L   V   V   Y   A   K   N   K   R   P   S   G   I   P   D   R 80         190        200        210        220        230        240
         ----------|----------|----------|----------|----------|----------|
Query  : TTCTCTGGCTCCAGCTCGGGAAACACAGCTTCCTTGACCATCACTGGGGCTCAGGCGGAA
Frame1 : F   S   G   S   S   S   G   N   T   A   S   L   T   I   T   G   A   Q   A   E 40         250        260        270        280        290        300
         ----------|----------|----------|----------|----------|----------|
Query  : GATGAGGCTGACTATTACTGTCATTCCCGGGACAGCGGTGGTAACCATGTGCTTTTCGGC
Frame1 : D   E   A   D   Y   Y   C   H   S   R   D   S   G   G   N   H   V   L   F   G 310        320
         ----------|----------|---- 324
Query  : GGAGGGACCAAGCTGACCGTCCTA
Frame1 : G   G   T   K   L   T   V   L
```

Figure 5A
Ab-5 VH Domain

```
              10         20         30         40         50         60
         ----------|----------|----------|----------|----------|----------|
Query  : caggtgcagctggtgcagtctggggctgaggtgaagaagcctggggcctcagtgaaggtc
Frame1 : Q   V   Q   L   V   Q   S   G   A   E   V   K   K   P   G   A   S   V   K   V 70         80         90        100        110        120
         ----------|----------|----------|----------|----------|----------|
Query  : tcctgcaaggcttctggttacacctttaccggccagtacatccactgggtgcgacaggcc
Frame1 : S   C   K   A   S   G   Y   T   F   T   G   Q   Y   I   H   W   V   R   Q   A 20        130        140        150        160        170        180
         ----------|----------|----------|----------|----------|----------|
Query  : cctggacaagggcttgagtggatgggatggatcagcgcttacaatggttacacagactat
Frame1 : P   G   Q   G   L   E   W   M   G   W   I   S   A   Y   N   G   Y   T   D   Y 80        190        200        210        220        230        240
         ----------|----------|----------|----------|----------|----------|
Query  : gcacagaaggtccagggcagagtcaccatgaccacagacacatccaccagcacagcctac
Frame1 : A   Q   K   V   Q   G   R   V   T   M   T   T   D   T   S   T   S   T   A   Y 40        250        260        270        280        290        300
         ----------|----------|----------|----------|----------|----------|
Query  : atggagctgaggagcctgagatctgacgacacggccgtgtattactgtgcgagagagctg
Frame1 : M   E   L   R   S   L   R   S   D   D   T   A   V   Y   Y   C   A   R   E   L 310        320        330        340        350        360
         ----------|----------|----------|----------|----------|----------|
Query  : tggccagtggcagcagctgatacattcagtgttttttgatatctggggccgaggaaccctg
Frame1 : W   P   V   A   A   A   D   T   F   S   V   F   D   I   W   G   R   G   T   L 60        370
         ----------|----- 375
Query  : gtcaccgtctcgagt
Frame1 : V   T   V   S   S
```

Figure 5B
Ab-5 VL Domain

```
              10        20        30        40        50        60
         ----------|---------|---------|---------|---------|---------|
Query  : TCGTCTGAGCTGACTCAGGACCCTGCTGTGTCTGTGGCCTTGGGACAGACAGTCAGGATC
Frame1 :  S  S  E  L  T  Q  D  P  A  V  S  V  A  L  G  Q  T  V  R  I 70        80        90       100       110       120
         ----------|---------|---------|---------|---------|---------|
Query  : ACATGCCAAGGAGACAGCCTCAGAAGCTATTATGCAAGCTGGTACCAGCAGAAGCCAGGA
Frame1 :  T  C  Q  G  D  S  L  R  S  Y  Y  A  S  W  Y  Q  Q  K  P  G 20       130       140       150       160       170       180
         ----------|---------|---------|---------|---------|---------|
Query  : CAGGCCCCTGTACTTGTCATCTATGGTAAAAACAACCGGCCCTCAGGGATCCCAGACCGA
Frame1 :  Q  A  P  V  L  V  I  Y  G  K  N  N  R  P  S  G  I  P  D  R 80       190       200       210       220       230       240
         ----------|---------|---------|---------|---------|---------|
Query  : TTCTCTGGCTCCAGCTCAGGAAACACAGCTTCCTTGACCATCACTGGGGCTCAGGCGGAA
Frame1 :  F  S  G  S  S  S  G  N  T  A  S  L  T  I  T  G  A  Q  A  E 40       250       260       270       280       290       300
         ----------|---------|---------|---------|---------|---------|
Query  : GATGAGGCTGACTATTACTGTAACTCGCGGGACAGCAGTGGTAACCATGTGGTATTCGGC
Frame1 :  D  E  A  D  Y  Y  C  N  S  R  D  S  S  G  N  H  V  V  F  G 310       320
         ----------|---------|---- 324
Query  : GGAGGGACCAAGCTGACCGTCCTA
Frame1 :  G  G  T  K  L  T  V  L
```

Figure 6A
Ab-6 VH Domain

```
              10         20         30         40         50         60
     ---------|----------|----------|----------|----------|----------|
Query  : GAGGTGCAGCTGTTGGAGTCTGGGGGAGGCTTGGTACAGCCTGGGGGGTCCCTGAGACTC
Frame1 : E  V  Q  L  L  E  S  G  G  G  L  V  Q  P  G  G  S  L  R  L 70         80         90        100        110        120
     ---------|----------|----------|----------|----------|----------|
Query  : TCCTGTGCAGCCTCTGGATTCACCTTTAGCAGCTATGCCATGAGCTGGGTCCGCCAGGCT
Frame1 : S  C  A  A  S  G  F  T  F  S  S  Y  A  M  S  W  V  R  Q  A 20        130        140        150        160        170        180
     ---------|----------|----------|----------|----------|----------|
Query  : CCAGGGAAGGGGCTGGAGTGGGTCTCAGCTATTAGTGGTAGTGGTGGTAGCACATACTAC
Frame1 : P  G  K  G  L  E  W  V  S  A  I  S  G  S  G  G  S  T  Y  Y 80        190        200        210        220        230        240
     ---------|----------|----------|----------|----------|----------|
Query  : GCAGACTCCGTGAAGGGCCGGTTCACCATCTCCAGAGACAATTCCAAGAACACGCTGTAT
Frame1 : A  D  S  V  K  G  R  F  T  I  S  R  D  N  S  K  N  T  L  Y 40        250        260        270        280        290        300
     ---------|----------|----------|----------|----------|----------|
Query  : CTGCAAATGAACAGCCTGAGAGCCGAGGACACGGCCGTGTATTACTGTGCGAGAGATGGG
Frame1 : L  Q  M  N  S  L  R  A  E  D  T  A  V  Y  Y  C  A  R  D  G 310        320        330        340        350
     ---------|----------|----------|----------|----------|---- 354
Query  : AGGACGGGTTGCATGACTCCTGGGGCCAAGGGACAATGGTCACCGTCTCGAGT
Frame1 : R  T  G  C  L  H  D  S  W  G  Q  G  T  M  V  T  V  S  S
```

Figure 6B
Ab-6 VL Domain

```
                10         20         30         40         50         60
         ----------|----------|----------|----------|----------|----------|
Query  : CAGTCTGTGTTGACGCAGCCGCCCTCAGCGTCTGGGACCCCCGGACAGAGGGTCACTATC
Frame1 : Q   S   V   L   T   Q   P   P   S   A   S   G   T   P   G   Q   R   V   T   I 70         80         90        100        110        120
         ----------|----------|----------|----------|----------|----------|
Query  : TCTTGTTCTGGAAGCAGTTCCAACGTCGGAAGTAATTTTGTATATTGGTACCAGCAGTTC
Frame1 : S   C   S   G   S   S   S   N   V   G   S   N   F   V   Y   W   Y   Q   Q   F 20         130        140        150        160        170        180
         ----------|----------|----------|----------|----------|----------|
Query  : CCAGGAACGGCCCCCAAACTCCTCATCTATAGGAATAATCAGCGGCCCTCAGGGGTCCCT
Frame1 : P   G   T   A   P   K   L   L   I   Y   R   N   N   Q   R   P   S   G   V   P 80         190        200        210        220        230        240
         ----------|----------|----------|----------|----------|----------|
Query  : GACCGATTCTCTGGCTCCAAGTCCGGCACCTCAGCCTCCCTGGCCATTAGTGGCCTCCGG
Frame1 : D   R   F   S   G   S   K   S   G   T   S   A   S   L   A   I   S   G   L   R 40         250        260        270        280        290        300
         ----------|----------|----------|----------|----------|----------|
Query  : TCCGAGGATGAGGCTGATTATTACTGTGCAGCATGGGATGACACGCTGAATGGTCACTAC
Frame1 : S   E   D   E   A   D   Y   Y   C   A   A   W   D   D   T   L   N   G   H   Y 310        320        330
         ----------|----------|----------|--- 333
Query  : GTGTTCGGCGGAGGGACCAAGCTGACCGTCCTA
Frame1 : V   F   G   G   G   T   K   L   T   V   L
```

Figure 7A
Ab-7 VH Domain

```
                10        20        30        40        50        60
         ---------|---------|---------|---------|---------|---------|
Query  : GAGGTCCAGCTGGTGCAGTCTGGAGCAGAGGTGAAAAAGCCCGGGGAGTCTCTGAAGATC
Frame1 : E  V  Q  L  V  Q  S  G  A  E  V  K  K  P  G  E  S  L  K  I 70        80        90       100       110       120
         ---------|---------|---------|---------|---------|---------|
Query  : TCCTGTAAGGGATATGGATACGATTTCAGTCGCGACTGGATCGCCTGGGTGCGCCAGATG
Frame1 : S  C  K  G  Y  G  Y  D  F  S  R  D  W  I  A  W  V  R  Q  M 20       130       140       150       160       170       180
         ---------|---------|---------|---------|---------|---------|
Query  : CCCGGGAAAGGCCTGGAGTGGATGGGGATCATCTATCCTGGTGACTCTGATACCAGATAC
Frame1 : P  G  K  G  L  E  W  M  G  I  I  Y  P  G  D  S  D  T  R  Y 80       190       200       210       220       230       240
         ---------|---------|---------|---------|---------|---------|
Query  : AGCCCGTCCTTCGAAGGCCAGGTCACCATCTCAGCCGACAAGTCCATCAGCACCGCCTAC
Frame1 : S  P  S  F  E  G  Q  V  T  I  S  A  D  K  S  I  S  T  A  Y 40       250       260       270       280       290       300
         ---------|---------|---------|---------|---------|---------|
Query  : CTGCAGTGGAGAAGCCTGAAGGCCTCGGACACCGCCATGTATTACTGTGCGAGACAACGG
Frame1 : L  Q  W  R  S  L  K  A  S  D  T  A  M  Y  Y  C  A  R  Q  R 310       320       330       340       350
         ---------|---------|---------|---------|---------|---- 354
Query  : AGGTTGGGGTGGTTCGACCCCTGGGGCCAGGGGACAATGGTCACCGTCTCTTCA
Frame1 : R  L  G  W  F  D  P  W  G  Q  G  T  M  V  T  V  S  S
```

Figure 7B
Ab-7 VL Domain

```
                10        20        30        40        50        60
       ---------|---------|---------|---------|---------|---------|
Query : CGGTCTGTGTTGACGCAGCCGCCCTCAGTGTCTGCGGCCCCAGGACAGAAGGTCACCATT
Frame1: R   S   V   L   T   Q   P   P   S   V   S   A   A   P   G   Q   K   V   T   I 70        80        90       100       110       120
       ---------|---------|---------|---------|---------|---------|
Query : TCCTGCTCTGGAAGCACCTCCAACATTGGGAATAATTATGTCTCCTGGTACCAACAGCAC
Frame1: S   C   S   G   S   T   S   N   I   G   N   N   Y   V   S   W   Y   Q   Q   H 20       130       140       150       160       170       180
       ---------|---------|---------|---------|---------|---------|
Query : CCAGGCAAAGCCCCCAAACTCATGATTTATGATGTCAGTAAGGGGCCCTCAGGGGTCCCT
Frame1: P   G   K   A   P   K   L   M   I   Y   D   V   S   K   R   P   S   G   V   P 80       190       200       210       220       230       240
       ---------|---------|---------|---------|---------|---------|
Query : GACCGATTCTCTGGCTCCAAGTCTGGCAACTCAGCCTCCCTGGACATCAGTGGGCTCCAG
Frame1: D   R   F   S   G   S   K   S   G   N   S   A   S   L   D   I   S   G   L   Q 40       250       260       270       280       290       300
       ---------|---------|---------|---------|---------|---------|
Query : TCTGAGGATGAGGCTGATTATTACTGTGCAGCATGGGATGACAGCCTCAGTGAATTTCTC
Frame1: S   E   D   E   A   D   Y   Y   C   A   A   W   D   D   S   L   S   E   F   L 310       320       330
       ---------|---------|---------| 330
Query : TTCGGAACTGGGACCAAGCTGACCGTCCTA
Frame1: F   G   T   G   T   K   L   T   V   L
```

Figure 8A
Ab-8 VH Domain

```
                10         20         30         40         50         60
         ----------|----------|----------|----------|----------|----------|
Query  : GAGGTGCAGCTGTTGGAGTCTGGGGGAGGCTTGGTACAGCCTGGGGGGTCCCTGAGACTC
Frame1 : E   V   Q   L   L   E   S   G   G   G   L   V   Q   P   G   G   S   L   R   L 70         80         90        100        110        120
         ----------|----------|----------|----------|----------|----------|
Query  : TCCTGTGCAGCCTCTGGATTCACCTTTAGCAGCTATGCCATGAGCTGGGTCCGCCAGGCT
Frame1 : S   C   A   A   S   G   F   T   F   S   S   Y   A   M   S   W   V   R   Q   A 20        130        140        150        160        170        180
         ----------|----------|----------|----------|----------|----------|
Query  : CCAGGGAAGGGGCTGGAGTGGGTCTCAGCTATTAGTGGTAGTGGTGGTAGCACATACTAC
Frame1 : P   G   K   G   L   E   W   V   S   A   I   S   G   S   G   G   S   T   Y   Y 80        190        200        210        220        230        240
         ----------|----------|----------|----------|----------|----------|
Query  : GCAGACTCCGTGAAGGGCCGGTTCACCATCTCCAGAGACAATTCCAAGAACACGCTGTAT
Frame1 : A   D   S   V   K   G   R   F   T   I   S   R   D   N   S   K   N   T   L   Y 40        250        260        270        280        290        300
         ----------|----------|----------|----------|----------|----------|
Query  : CTGCAAATGAACAGCCTGAGAGCCGAGGACACGGCCGTGTATTACTGTGCGAGACATTTA
Frame1 : L   Q   M   N   S   L   R   A   E   D   T   A   V   Y   Y   C   A   R   H   L 310        320        330        340        350        360
         ----------|----------|----------|----------|----------|----------|
Query  : CCGTCTGGGTCTAGCAGCAGTTGGGCCTTTGACTCCTGGGGGCGAGGGACCACGGTCACC
Frame1 : P   S   G   S   S   S   S   W   A   F   D   S   W   G   R   G   T   T   V   T 60
         ---------- 369
Query  : GTCTCGAGT
Frame1 : V   S   S
```

Figure 8B
Ab-8 VL Domain

```
              10        20        30        40        50        60
         ---------|---------|---------|---------|---------|---------|
Query  : TCCTATGTGCTGACTCAGCCACCCTCAGCGTCTGGGACCCCCGGGCAGAGGGTCACCATC
Frame1 : S  Y  V  L  T  Q  P  P  S  A  S  G  T  P  G  Q  R  V  T  I 70        80        90       100       110       120
         ---------|---------|---------|---------|---------|---------|
Query  : TCTTGTTCTGGAAGCAGCTCCAACATCGGAAGTAATTATGTATACTGGTACCAGCAGCTC
Frame1 : S  C  S  G  S  S  S  N  I  G  S  N  Y  V  Y  W  Y  Q  Q  L 20       130       140       150       160       170       180
         ---------|---------|---------|---------|---------|---------|
Query  : CCAGGAACGGCCCCCAAACTCCTCATCTATAGGAATAATCAGCGGCCCTCAGGGGTCCCT
Frame1 : P  G  T  A  P  K  L  L  I  Y  R  N  N  Q  R  P  S  G  V  P 80       190       200       210       220       230       240
         ---------|---------|---------|---------|---------|---------|
Query  : GACCGATTCTCTGGCTCCAAGTCTGGCACCTCAGCCTCCCTGGCCATCAGTGGGCTCCAG
Frame1 : D  R  F  S  G  S  K  S  G  T  S  A  S  L  A  I  S  G  L  Q 40       250       260       270       280       290       300
         ---------|---------|---------|---------|---------|---------|
Query  : TCTGAGGATGAGGCTGATTATTACTGTGAGGCATGGGATGACAACGTCGATGGTCCGGTC
Frame1 : S  E  D  E  A  D  Y  Y  C  E  A  W  D  D  N  V  D  G  P  V 310       320       330
         ---------|---------|---------| 330
Query  : TTCGGCGGGGGGACCAAGCTGACCGTCCTA
Frame1 : F  G  G  G  T  K  L  T  V  L
```

ANTIBODIES OF ANGIOGENESIS INHIBITING DOMAINS CD148

CROSS-REFERENCE TO RELATED APPLICATIONS

This application claims the benefit of U.S. Provisional Application No. 60/564,885, filed Apr. 23, 2004; U.S. Provisional Application No. 60/565,158, filed Apr. 23, 2004; U.S. Provisional Application No. 60/571,566, filed May 14, 2004; and U.S. Provisional Application No. 60/585,686, filed Jul. 6, 2004.

TECHNICAL FIELD OF THE INVENTION

The present invention relates to anti-CD148 antibodies and to binding epitopes of CD148 used to produce such antibodies. The invention also relates to methods of using such antibodies to inhibit angiogenesis.

BACKGROUND OF THE INVENTION

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular diseases, arthritis, and psoriasis, the process can go awry. Folkman, J., Nat. Med., 1:27-31 (1995).

Angiogenesis is believed to play an important role in sustaining inflammatory tissue expansion (pannus) in rheumatoid arthritis (Walsh et al., Arthritis Res., 3:147-153 (2001). In fact, there are a number of diseases known to be associated with deregulated or undesired angiogenesis. See Carmeliet et al., Nature 407:249-257 (2000). Such diseases include, but are not limited to, ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid (or hematopoietic) tumors (such as leukemias and lymphomas). Other diseases associated with undesired angiogenesis will be apparent to those skilled in the art.

Although many signal transduction systems have been implicated in the regulation of angiogenesis, one recently-characterized endothelial cell systems involves the the CD148 receptor tyrosine kinase (also referred to as DEP-1 (density enhanced phosphatase), ECRTP (endothelial cell receptor tyrosine phosphatase), HPTPη, or BYP, depending upon species and cDNA origin).

CD148 is a mammalian transmembrane protein, belonging to a class of endothelial cell surface receptors known as Type III density enhanced receptor protein tyrosine phosphatases (PTP). Protein tyrosine phosphorylation is an essential element in signal transduction pathways which control fundamental cellular processes including growth and differentiation, cell cycle progression, and cytoskeletal function. Binding of a ligand to a receptor protein tyrosin kinase (PTK) catalyzes autophosphorylation of tyrosine residues in the enzyme's target substrates, while binding of a ligand to a receptor PTP catalyzes dephosphorylation. The level of intracellular tyrosine phosphorylation of a target substrate is determined by the balance between PTK and PTP. PTKs play a significant role in promoting cell growth, while PTPs downregulate the activity of PTKs by inhibiting cell growth. CD148 has been shown to promote differentiation of erythroid progentior cells, modulate lymphocyte function when crosslinked with other signaling proteins, and inhibit clonal expression of breast cancer cell lines overexpressing the protein. Confirming its role as an inhibitor of cell growth, CD148 has also recently been shown to mediate inhibitory signals that block angiogenesis, an essential biological activity necessary for cell migration and proliferation, making CD148 an important target for treatment of cancer by activating CD148 mediated inhibitiion of angiogenesis associated with tumor growth.

Like other receptor protein tyrosine phosphatases, CD148 has an intracellular carboxyl moiety with a catalytic domain, a single transmambrane domain, and an extracellular amino terminal domain (comprising five tandem fibronectin type III (FNIII) repeats, which have a folding pattern similar to that of Ig-like domains). The FNIII domains have an absolute specificity for phosphotyrosine residues, a high affinity for substrate proteins, and a specific activity which is several orders of magnitude greater than that of the PTKs. The FNIII domains are believed to participate in protein/protein interactions to Activation of CD148 triggers autophosphorylation of CD148, which tranduces a biological signal resulting in inhibition of angiogenesis.

U.S. Pat. No. 6,552,169 discloses polynucleotide sequences relating to human DEP-1 (CD148) and polyclonal antibodies generated against polypeptides encoded by the polynucleotides.

U.S. Pat. No. 6,248,327 discloses the role of CD148 in angiogenesis and provides a method of modulating angiogenesis in a mammal by administering compositions that specifically bind to the ectodomain of CD148, and also discloses the use of monoclonal antibodies that specifically bind to an unspecified region of the CD148 ectodomain to activate CD148 anti-angiogenesis activity.

An effective CD148 activation therapy might benefit a vast population of cancer patients because most solid tumors require neovascularization to grow beyond 1-2 millimeters in diameter. Such therapy might have wider application in other angiogenesis-associated diseases as well, such as retinopathies, arthritis, and psoriasis.

There is an undeveloped need to identify new agents that specifically recognize and bind CD148. Such agents would be useful for diagnostic screening and therapeutic intervention in disease states that are associated with CD148 activity.

Accordingly, it is an object of the present invention to provide specific binding agents of CD148 that activate CD148 activity. Such agents of the present invention take the form of antibodies and fragments thereof that specifically bind to CD148 epitopes.

The disclosure all patents, patent applications, and other documents cited herein are hereby expressly incorporated by reference in their entirety.

SUMMARY OF THE INVENTION

The present invention provides anti-CD148 antibodies, or antigen-binding regions thereof, that bind to CD148 epitopes involved in inhibition of inflammation and/or angiogenesis, which antibodies can be used for treatment of inflammation and angiogenesis related diseases. In particular embodiments, the antibodies or antigen-binding regions thereof are dervied from human antibodies or antigen-binding regions thereof. In other embodiments, the antibodies or antigen-binding fragments thereof are selected from the group consisting of scFv, Fab, F(ab')$_2$, Fv, and single chain antibodies, and can in particular be scFv fragments, and more particularly an scFv-Fc fusion. In another particular embodiment, the antibody or antigen-binding region thereof is a in IgG isotype, such as an IgG2 isotype.

One aspect of the presention invention provides isolated antibodies or antigen-binding regions thereof that bind to a CD148 epitope defined by FNIII domains 2, 3, 4 or 5 of CD148. In a particular embodiment, the antibodies of the present invention include isolated antibodies or antigen-binding regions thereof that specifically bind to a human CD148 epitope defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33. In yet another embodiment, the antibodies of the present invention include isolated antibodies or antigen-binding regions thereof that competitively inhibit binding of the above monoclonal antibodies to a human CD148 epitope defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33. In a more particular embodiment, the antibodies of the present invention include isolated antibodies or antigen-binding regions thereof that specifically bind to a human CD148 epitope defined by one or more of the polypeptide sequences selected from the group consisting of amino acids 324-338 and 321-335 of SEQ ID NO:33, but which does not bind to the polypeptide sequence of amino acid residues 324-331 of SEQ ID NO:33. Examples of such antibodies include antibodies Ab-1, Ab-2, Ab-3, Ab-4, Ab-5, Ab-6, Ab-7, and Ab-8.

Another aspect of the present invention provides hybridoma cells and transfectoma cells which produces the antibody or antigen binding region thereof of the present invention, and antibodies or antigen-binding region thereof produced by such hybridoma and transfectoma cells. A hybridoma may include a B cell obtained from a transgenic non-human animal having a genome comprising a human heavy chain transgene and a human light chain transgene fused to an immortalized cell. A transfectoma may include nucleic acids encoding a human heavy chain and a human light chain.

Another aspect of the present invention provides a transgenic non-human animal which expresses the antibody or antigen-binding region thereof of the present invention, wherein the transgenic non-human animal has a genome comprising a human heavy chain transgene and a human light chain transgene.

Another aspect of the present invention provides a method of producing an antibody or antigen binding region thereof that specifically binds to a human CD148 epitope defined by one or more of the sequence of amino acids selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, comprising: immunizing a transgenic non-human animal having a genome comprising a human heavy chain transgene and a human light chain transgene with a human CD148 epitope defined by one or more of the sequence of amino acids selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, or a cell expressing such human CD148 epitope, such that antibodies are produced by B cells of the animal; isolating B cells of the animal; and fusing the B cells with myeloma cells to form immortal, hybridoma cells that secrete the antibody or antigen binding region thereof.

Another aspect of the present invention provides a pharmaceutical composition comprising the antibody or antigen binding region thereof of the antibodies or antigen-binding regions thereof and a carrier pharmaceutically acceptable in humans. A particular embodiment provides an antibody or antigen binding region thereof present in a therapeutically effective amount, such as in a concentration of at least about 10 µg/ml.

Another aspect of the present invention provides a a method for inhibiting angiogenesis comprising administering to a patient in need thereof a therapeutically effective amount of an antibody or antigen-binding region thereof of the present invention.

Another aspect of the present invention provides CD148 epitopes, binding to which activates CD148 mediated biological activity. CD148 epitopes of the present invention include isolated polypeptides comprising one or more of the amino acid sequencs selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, or any fragment thereof that binds to an antibody or antigen-binding region thereof of the present invention, wherein the polypeptide does not include amino acids derived from CD148 other than those selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33. In another embodiment, the present invention provides an isolated polypeptide consisting of one or more of the amino acid sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33 or any fragment thereof that binds to an antibody or antigen-binding region thereof of the present invention. In yet another embodiment, the present invention provides an isolated polypeptide consisting essentially of one or more of the amino acid sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33 or any fragment thereof that binds to an antibody or antigen-binding region thereof of the present invention.

Another aspect of the present invention provides an immunoassay comprising the steps of: (a) contacting a test sample with a monoclonal antibody or antigen-binding region thereof capable of being competitively inhibited in its binding to human CD148 by a monoclonal antibody or antigen-binding region thereof that specifically binds to a human CD148 epitope defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33 or any fragment thereof that binds to an antibody or antigen-binding region thereof of the present invention; and (b) determining the presence of human CD148 in the test sample.

Another aspect of the invention includes a method for identifying a compound that specifically binds to a human CD148 epitope defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, comprising: contacting a test compound with a human CD148 epitope defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33 for a time sufficient to form a complex and detecting for the formation of a complex by detecting the CD148 epitope or the compound in the complex, so that if a complex is detected, a compound that binds to the CD148 epitope is identified.

Yet another aspect of the present invention is a method for identifying a compound that specifically binds to a human CD148 epitope defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, comprising: providing atomic coordinates defining a three-dimensional structure of a CD148 epitope defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, and designing or selecting compounds capable of binding the CD148 epitope based on said atomic coordinates.

DESCRIPTION OF THE FIGURES

FIGS. 1A and 1B show a nucleotide and encoded amino acid sequence overlap for variable heavy (VH) and variable light (VL) chains for an antibody of the present invention, Antibody No. 1 (Ab-1). Shaded regions on the figure highlight CDR1, 2, and 3 (from amino to carboxy terminus, respectively). Query and Frame1 designations indicate the nucleotide and amino acid sequences, respectively.

FIGS. 2A and 2B show a nucleotide and encoded amino acid sequence overlap for variable heavy (VH) and variable light (VL) chains for Antibody No. 2 (Ab-2). Shaded regions on the figure highlight CDR1, 2, and 3 (from amino to carboxy terminus, respectively).

FIGS. 3A and 3B show a nucleotide and encoded amino acid sequence overlap for variable heavy (VH) and variable light (VL) chains for Antibody No. 3 (Ab-3). Shaded regions on the figure highlight CDR1, 2, and 3 (from amino to carboxy terminus, respectively).

FIGS. 4A and 4B show a nucleotide and encoded amino acid sequence overlap for variable heavy (VH) and variable light (VL) chains for Antibody No. 4 (Ab-4). Shaded regions on the figure highlight CDR1, 2, and 3 (from amino to carboxy terminus, respectively).

FIGS. 5A and 5B show a nucleotide and encoded amino acid sequence overlap for variable heavy (VH) and variable light (VL) chains for Antibody No. 5 (Ab-5). Shaded regions on the figure highlight CDR1, 2, and 3 (from amino to carboxy terminus, respectively).

FIGS. 6A and 6B show a nucleotide and encoded amino acid sequence overlap for variable heavy (VH) and variable light (VL) chains for Antibody No. 6 (Ab-6). Shaded regions on the figure highlight CDR1, 2, and 3 (from amino to carboxy terminus, respectively).

FIGS. 7A and 7B show a nucleotide and encoded amino acid sequence overlap for variable heavy (VH) and variable light (VL) chains for Antibody No. 7 (Ab-7). Shaded regions on the figure highlight CDR1, 2, and 3 (from amino to carboxy terminus, respectively).

FIGS. 8A and 8B show a nucleotide and encoded amino acid sequence overlap for variable heavy (VH) and variable light (VL) chains for Antibody No. 8 (Ab-8). Shaded regions on the figure highlight CDR1, 2, and 3 (from amino to carboxy terminus, respectively).

DETAILED DESCRIPTION OF THE INVENTION

In order that the present invention may be more readily understood, certain terms are first defined. Additional definitions are set forth throughout the detailed description.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of". The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "human CD148" is the protein identified as human ECRTP/DEP in Ostman et al., *Proc Natl Acad Sci USA* 91:9680-9684 (1994), incorporated by reference herein, including allelic variants thereof. By "extracellular domain of human CD148" is meant the portion of human CD148 localized between about residues 36 to 973 (residues 1 to 35 being the leader sequence and not present in the mature form) of NCBI (National Center for Biotechnology Information) accession AAB36687 version AAB36687.1 GI:1685075, submitted Nov. 26, 1996, incorporated by reference herein and available on the world wide web at ncbi.nlm.nih.gov.

The term "antibody" includes both glycosylated and non-glycosylated immunoglobulins of any isotype or subclass or combination thereof, including human (including CDR-grafted antibodies), humanized, chimeric, multi-specific, monoclonal, polyclonal, and oligomers thereof, irrespective of whether such antibodies are produced, in whole or in part, via immunization, through recombinant technology, by way of in vitro synthetic means, or otherwise. Thus, the term "antibody" includes those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such antibodies have variable and constant regions derived from germline immunoglobulin sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the VH and VL regions of the antibodies are sequences that, while derived from and related to the germline VH and VL sequences of a particular species (e.g., human), may not naturally exist within that species' antibody germline repertoire in vivo.

A whole antibody is a glycoprotein comprising at least two heavy (H) chains and two light (L) chains inter-connected by disulfide bonds, or an antigen-binding region thereof. Each heavy chain is comprised of a heavy chain variable region (abbreviated herein as VH) and a heavy chain constant region, comprised of three domains (abbreviated herein as CH1, CH2 and CH3). Each light chain is comprised of a light chain variable region (abbreviated herein as VL) and a light chain constant region, comprised of one domain (abbreviated herein as CL). The VH and VL regions can be further subdivided into regions of hypervariability, termed complementarily determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An amino acid sequence which is substantially the same as a heavy or light chain CDR exhibits a considerable amount or extent of sequence identity when compared to a reference sequence and contributes favorably to specific binding of an antigen bound specifically by an antibody having the reference sequence. Such identity is definitively known or recognizable as representing the amino acid sequence of the particular human monoclonal antibody. Substantially the same heavy and light chain CDR amino acid sequence can have, for example, minor modifications or conservative substitutions of amino acids so long as the ability to bind a particular antigen is maintained. The term "human monoclonal antibody" is intended to include a monoclonal antibody with substantially human CDR amino acid sequences produced, for example, by recombinant methods, by lymphocytes or by hybridoma cells.

The term "antigen-binding region" of an antibody means one or more fragments of an antibody that retain the ability to specifically bind to an antigen (e.g., CD148) that is specifically bound by a reference antibody, as disclosed herein. An "antigen-binding regions" of an antibody may include, for example, polypeptides comprising individual heavy or light chains and fragments thereof, such as VL, VH and Fd regions; monovalent fragments, such as Fv, Fab, and Fab' regions; bivalent fragments such as F(ab')$_2$; single chain antibodies, such as single chain Fv (scFv) regions; Fc fragments; diabodies; Fd (consisting of the VH and CH1 domains), maxibodies (bivalent scFV fused to the amino terminus of the Fc (CH2-CH3 domains) of IgG1) and complementarity determining region (CDR) domains. Such terms are described, for example, in Harlow and Lane, Antibodies: A Laboratory Manual, Cold Spring Harbor Laboratory, N.Y. (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, N.Y. (1990), which are incorporated herein by reference. The term "antigen-binding region" also includes, for example, fragments produced by protease digestion or reduction of a human monoclonal antibody and by recombinant DNA methods known to those skilled in the art. One skilled in the art knows that the exact boundaries of a fragment of a human monoclonal antibody can be variable, so long as the fragment maintains a functional activity. Using well-known recombinant methods, one skilled in the art can engineer a nucleic acid to express a functional fragment with any endpoints desired for a particular application. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding region" of an antibody. These antibody fragments are obtained using conventional techniques known to those with skill in the art, and the fragments are screened for utility in the same manner as are intact antibodies. Such fragments include those obtained by amino-terminal and/or carboxy-terminal deletions, but where the remaining amino acid sequence is substantially identical to the corresponding positions in the naturally-occurring sequence deduced, for example, from a full-length cDNA sequence. Antigen binding regions also include fragments of an antibody which retain at least one (e.g., 1, 2, 3 or more) heavy chain sequences and/or at least one (e.g., 1, 2, 3 or more) light chain sequences for a particular complementarity determining region (CDR) (i.e., at least one or more of CDR1, CDR2, and/or CDR3 from the heavy and/or light chain). Fusions of CDR containing sequences to an Fc region (or a constant heavy 2 (CH2) or constant heavy 3 (CH3) containing region thereof) are included within the scope of this definition including, for example, scFV fused, directly or indirectly, to an Fc are included herein. An antigen binding region is inclusive of, but not limited to, those derived from an antibody or fragment thereof (e.g., by enzymatic digestion or reduction of disulfide bonds), produced synthetically using recombinant methods (e.g., transfectomas), created via in vitro synthetic means (e.g., Merrifield resins), combinations thereof, or through other methods. Antigen-binding regions may also comprise multiple fragments, such as CDR fragments, linked together synthetically, chemically, or otherwise, in the form of oligomers. Thus, antigen binding regions of the present invention include polypeptides produced by any number of methods which comprise at least one CDR from a VH or VL chain of the present invention (e.g., Ab-1 through Ab-8).

The term "$V_L$ fragment" means a fragment of the light chain of a human monoclonal antibody which includes all or part of the light chain variable region, including the CDRs. A VL fragment can further include light chain constant region sequences.

The term "Fd fragment" means a fragment of the heavy chain of a human monoclonal antibody which includes all or part of the VH heavy chain variable region, including the CDRS. An Fd fragment can further include CH1 heavy chain constant region sequences.

The term "Fv fragment" means a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" means a monovalent antigen-binding fragment of an antibody consisting of the VL, VH, CL and CH1 domains, which is larger than an Fv fragment. For example, an Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" means a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "$F(ab')_2$ fragment" means a bivalent antigen-binding fragment of a human monoclonal antibody comprising two Fab fragments linked by a disulfide bridge at the hinge region. An $F(ab')_2$ fragment includes, for example, all or part of the variable regions of two heavy chains and two light chains, and can further include all or part of the first constant domains of two heavy chains and two light chains.

The term "dAb fragment" means a fragment consisting of the VH domain, as described by Ward et al., (1989) Nature 341:544-546).

The term "CDR" means the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987) and additionally by MacCallum et al., J. Mol. Biol. 262:732-745 (1996), which are incorporated herein by reference, where the definitions include overlapping or subsets of amino acid residues when compared against each other. Nevertheless, application of either definition to refer to a CDR of an antibody or functional fragment thereof is intended to be within the scope of the term as defined and used herein. The exact amino acid residue numbers which encompass a particular CDR will vary depending on the structure of the CDR. Those skilled in the art can routinely determine which residues comprise a particular CDR given the variable region amino acid sequence of the antibody. Those skilled in the art can compare two or more antibody sequences by defining regions or individual amino acid positions of the respective sequences with the same CDR definition.

The term "CDR-grafted" refers to an antibody or antigen binding region in which the CDRs derived from one species are inserted into the framework of a different species, such as murine CDRs grafted on a human framework (a "human" antibody).

The term "analog" means polypeptides which are comprised of a segment of at least 25 amino acids that has substantial identity to a portion of a deduced amino acid sequence and which has at least one of the following properties: (1) specific binding to CD148, under suitable binding conditions, (2) ability to block CD148 ligands from binding to CD148, or (3) ability to inhibit CD148 mediated angiogenesis. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

The term "isolated" means separated from one or more compound that is found with the antibody or polypeptide in nature or in a synthetic reaction used to produce the antibody including, for example, a reagent, precursor or other reaction product, and preferably substantially free from any other contaminating mammalian polypeptides that would interfere with its therapeutic or diagnostic use. An isolated agent also includes a substantially pure agent. The term can include naturally occurring molecules such as products of biosynthetic reactions or synthetic molecules. An antibody is also considered "isolated," for example, when it is substantially free of other antibodies having different antigenic specificities. Also, a substance is "isolated" if it is bound or conjugated to a polypeptide or other substance to which is is not bound in nature.

The term "substantially pure" means a substance that is the predominant species present (i.e., on a molar basis it is more abundant than any other individual species in the composition) and comprises at least about 50 percent (on a molar basis) of all macromolecular species present. Generally, a substantially pure composition will comprise more than about 80 percent of all macromolecular species present in the composition, or alternatively more than about 85%, 90%, 95%, and 99%. A substance is purified to essential homogeneity (contaminant species cannot be detected in the composition by conventional detection methods) wherein the composition consists essentially of a single macromolecular species. Similarly, a substance is "isolated" if in the course of manufacture or formulation it is "isolated" or "substantially pure" as described above, and then combined with other agents in a well-defined composition, notwithstanding the substance in the well-defined composition is not the predominant species present.

As used herein, the terms "specifically binds" and "specific binding" mean that a compound preferentially or selectively recognizes and binds mature, full-length or partial-length epitope of CD148, or an ortholog thereof, such that its affinity (as determined by, e.g., Affinity ELISA or BIAcore assays as described herein) or its neutralization capability (as determined by e.g., Neutralization ELISA assays described herein, or similar assays) is at least 10 times as great, but optionally 50 times as great, 100, 250 or 500 times as great, or even at least 1000 times as great as the affinity or neutralization capability of the same for any other polypeptide, wherein the peptide portion of the peptibody is first fused to a human Fc moiety for evaluation in such assay. Typically, the antibody binds with an affinity of at least about $1\times10^7$ $M^{-1}$, and binds to the predetermined antigen with an affinity that is at least two-fold greater than its affinity for binding to a non-specific antigen (e.g., BSA, casein) other than the predetermined antigen or a closely-related antigen. As used herein, an antibody "recognizing" or "specific for" an antigen is considered equivalent to "binding specifically" to an antigen. An antibody that specifically binds to a specified epitope, isoform or variant of human CD148 may, however, still have cross-reactivity to other related antigens, e.g., from other species (e.g., CD148 species homologs) and still be considered to "specifically bind" the specified CD148 epitope.

The term "epitope" refers to that portion of any molecule capable of being recognized by and bound by a specific binding agent, e.g., an antibody, at one or more of the binding agent's antigen binding regions. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. An antibody is considered to specifically bind an antigen when the dissociation constant is less than or equal to about 1 µM, preferably less than or equal to about 100 nM and most preferably less than 10 nM. The antibodies and antigen-binding regions of such antibodies of the present invention include antibodies and antigen-binding regions thereof that are generated using the eptitopic determinants defined herein, or that are generated using epitopic determinants having substantial identity to the eptitopic determinants defined herein. In this context, the term "substantial identity" means that the sequences share sufficient identity that an antibody that binds to the modified epitopic determinant competitively inhibits binding of an antibody to the epitopic determinants described herein.

The phrase "competitively inhibits binding" means that an antibody recognizes, binds to or has immunospecificity for the same, or substantially the same, epitope or fragment thereof as another antibody or antigen-binding region thereof. In the context of the present invention, an isolated antibody or antigen-binding region thereof that competitively inhibits binding of a monoclonal antibody that specifically binds to a human CD148 epitope defined by the sequence of amino acids selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, is able to measurably compete for binding to CD148. Typically, competitive inhibition is measured by determining the amount of a reference antibody or antigen binding region which is bound to the target protein (e.g., human CD148) in the presence of the tested antibody or antigen binding region thereof. Usually the tested antibody or tested antigen binding region is present in excess, such as 5-, 10-, 25-, or 50-fold excess. Competitively bound antibodies or antigen binding regions will, when present in excess, inhibit specific binding of a reference antibody or antigen binding region to the extracellular domain of human CD148 by a statistically significant degree, often at least 10%, 25%, 50%, 75%, 90% or greater. Competitive inhibition assays are well known in the art. See, for example, Harlow and Lane (1998), Antibodies, A Laboratory Manual, Cold Spring Harbor Publications, New York. As used herein, inhibition of binding encompasses both partial and complete inhibition/blocking. Inhibition and blocking are also intended to include any measurable decrease in the binding affinity of a particular anti-CD148 antibody to CD148 when in contact with an anti-CD148 antibody of the present invention, e.g., the blocking of binding by at least about 10%, 20%, 30%, 40%, 50%, 60%, 70%, 80%, 90%, 99%, or 100%.

The identification of one or more antibodies that competitively inhibits binding of a monoclonal antibody that specifically binds to a human CD148 epitope defined by the sequence of amino acids selected from the group consisting of amino acids 447-725, 533-725, 715-973, 324-335, 200-536, 533-725 and 200-725 of SEQ ID NO:33 is a straightforward technical matter given the determination of the above epitopes defined by such amino acids. Upon generation of an antibody that specifically binds to a human CD148 epitope defined by the sequence of amino acids selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33, identification of antibodies that competitively inhibit binding of those antibodies to CD148 is readily determined simply by comparison to the reference antibody.

The identification of cross-reactive antibodies can be readily determined using any one of variety of immunological screening assays in which antibody competition can be assessed. Such assays are routine in the art and are further described herein in detail. U.S. Pat. No. 5,660,827, issued Aug. 26, 1997, is specifically incorporated herein by reference for purposes including even further supplementing the present teaching concerning how to make antibodies that bind to the same or substantially the same epitope as a given antibody.

For example, where the test antibodies to be examined are obtained from different source animals, or are even of a different isotype, a simple competition assay may be employed in which the control and test antibodies are admixed (or pre-adsorbed) and applied to a CD148 antigen composition that contains a CD148 epitope as described herein. Thus, protocols based upon ELISAs and Western blotting are suitable for use in such simple competition studies.

In certain embodiments, one would or pre-mix the control antibodies with varying amounts of the test antibodies (e.g., 1:10 or 1:100) for a period of time prior to applying to an antigen composition. In other embodiments, the control and varying amounts of test antibodies can simply be admixed during exposure to the antigen composition. In any event, by using species or isotype secondary antibodies one will be able to detect only the bound control antibodies, the binding of which will be reduced by the presence of a test antibody that recognizes substantially the same epitope.

In conducting an antibody competition study between a control antibody and any test antibody (irrespective of species or isotype), one may first label the control with a detectable label, such as, e.g., biotin or an enzymatic (or even radioactive) label to enable subsequent identification. In these cases, one would pre-mix or incubate the labeled control antibodies with the test antibodies to be examined at various ratios (e.g., 1:10 or 1:100) and (optionally after a suitable period of time) then assay the reactivity of the labeled control antibodies and compare this with a control value in which no potentially competing test antibody was included in the incubation.

The assay may again be any one of a range of immunological assays based upon antibody hybridization, and the control antibodies would be detected by means of detecting their label, e.g., using streptavidin in the case of biotinylated antibodies or by using a chromogenic substrate in connection with an enzymatic label (such as 3,3'5,5'-tetramethylbenzidine (TMB) substrate with peroxidase enzyme) or by simply detecting a radioactive label. An antibody that binds to the same epitope as the control antibodies will be able to effectively compete for binding and thus will significantly reduce control antibody binding, as evidenced by a reduction in bound label.

The reactivity of the (labeled) control antibodies in the absence of a completely irrelevant antibody would be the control high value. The control low value would be obtained by incubating the labeled antibodies with unlabelled antibodies of exactly the same type, when competition would occur and reduce binding of the labeled antibodies. In a test assay, a significant reduction in labeled antibody reactivity in the presence of a test antibody is indicative of a test antibody that recognizes the same epitope, i.e., one that "cross-reacts" with the labeled antibody.

The phrase "inhibits angiogenesis" means a statistically significant reduction in the level of angiogenesis relative to an untreated control. Exemplary reductions are from at least 5 to 99%, and thus include at least 10%, 20%, 30%, 40%, 50%, 60%, 70%, 80%, or 90% reduction in angiogenesis relative to a negative control. Widely accepted functional assays of angiogenesis such as the corneal micropocket assay and the human renal microvascular endothelial cell (HRMEC) planar migration assay are known in the art. See, e.g., U.S. Pat. Nos. 5,712,291 and 5,871,723. Briefly, an HRMEC planar migration assay is a wound closure that assay can be used to quantitate the inhibition of angiogenesis by antibodies or antigen binding regions of the present invention in vitro. In this assay, endothelial cell migration is measured as the rate of closure of a circular wound in a cultured cell monolayer. The rate of wound closure is linear, and is dynamically regulated by agents that stimulate and inhibit angiogenesis in vivo. A mouse corneal pocket assay can also be used to quantitate the inhibition of angiogenesis by antibodies or antigen binding regions of the present invention in vivo. In this assay, agents to be tested for angiogenic or anti-angiogenic activity are immobilized in a slow release form in a hydron pellet, which is implanted into micropockets created in the corneal epithelium of anesthetized mice. Vascularization is measured as the appearance, density, and extent of vessel ingrowth from the vascularized corneal limbus into the normally avascular cornea.

It is understood that the antibodies of the present invention may be modified, such that they are substantially identical to the antibody polypeptide sequences, or fragements thereof, and still bind the CD148 epitopes of the present invention. Polypeptide sequences are "substantially identical" when, optimally aligned using such programs as GAP or BESTFIT using default gap weights, they share at least 80 percent sequence identity, at least 90 percent sequence identity, at least 95 percent sequence identity, or at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J.

Tooze, eds., Garland Publishing, New York, N.Y. (1991)); and Thornton et at. Nature 354:105 (1991), which are each incorporated herein by reference.

The antibodies of the present invention may also be generated using peptide analogs of the epitopic determinants disclosed herein, which analogs may consist of non-peptide compounds having properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH=CH-$ (cis and trans), $-COCH_2-$, $-CH(OH)CH_2-$, and $CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference); for example, by adding internal cysteine residues capable of forming intramolecular disulfide bridges which cyclize the peptide.

The term "bispecific molecule" is intended to include any agent, e.g., a protein, peptide, or protein or peptide complex, which has at least two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CD148 epitopes, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al (1993) Proc. Natl. Acad. Sci. USA 90:6444-6448; Poljak, R. J., et al. (1994) Structure 2:1121-1123). A bispecific antibody includes two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

The term "human antibody" refers to an antibody in which both the constant regions and the framework consist of fully or substantially human sequences such that the human antibody elicits substantially no immunogenic reaction against itself when administered to a human host and preferably, no detectable immunogenic reaction. It is to be understood that a "human antibody" need not consist entirely of human sequences, but may contain portions of non-human sequences, provided that the antibody does not elicit an immunogenic reaction when administered to the human host. For example, a "human antibody" includes antibodies in which CDR regions of non-human species, such as a mounse, are grafted on a human framework. In certain embodiments, human antibodies are produced in non-human mammals, including, but not limited to, mice, rats, and lagomorphs. In other embodiments, human antibodies are produced in hybridoma cells from transgenic animals having a human immunoglobulin repertoire. In other embodiments, fully human antibodies are produced recombinantly, such as in a transfectoma.

The term "humanized antibody" refers to an antibody in which substantially all of the constant region is derived from a human, while all or part of one or more variable regions is derived from another species, for example a mouse.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant", as used herein in reference to antibodies, is intended to include all human antibodies that are prepared, expressed, created or isolated by recombinant means, such as (a) antibodies isolated from an animal (e.g., a mouse) that is transgenic for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human theta-mu and human theta-mu (delta-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a mu switch region, will be 5' (i.e., upstream) of the construct region to be deleted during the switch recombination. The "switch acceptor" region will be between the construct region to be deleted and the replacement constant region (e.g., gamma, epsilon etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "transfectoma", as used herein, includes recombinant eukaryotic host cell expressing the antibody, such as CHO cells or NS/0 cells.

The terms "transgenic nonhuman animal" refers to a nonhuman animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD148 antibodies when immunized with CD148 and/or cells expressing CD148. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to CD148 (e.g., IgG, IgA and/or IgE) by undergoing V-D-J recombination and isotype switching.

Various aspects of the invention are described in further detail in the following subsections.

Production of Antibodies to CD148

The present invention is exemplified by antibodies or an antigen-binding regions thereof that bind to specified epitopes of CD148 that have been determined to play a role in activation of CD148 mediated inflammatory and/or angiogenic activity. Such antibodies or antigen-binding regions thereof of include anti-CD148 antibodies and antigen-binding regions thereof whose binding to CD148 can be competitively inhibited by the antibodies or antigen-binding regions thereof disclosed herein. The polynucleotide sequences encoding the antibodies and antigen-binding regions thereof of the present invention, as well as the polypeptide sequences expressed by such polynucleotide sequences, are disclosed in co-pending U.S. Provisional Patent Application Nos. 60/564,885 and 60/585,686, the contents of which are incorporated herein by reference in their entirety.

The present invention provides anti-CD148 antibodies that bind to substantially the same epitope as a human CD148 epitope defined by one or more of the polypeptide sequences selected from the group consisting of amino acids 447-725, 533-725, 715-973, 324-335, 200-536, 533-725 and 200-725 of SEQ ID NO:33. In another embodiment, the present invention provides anti-CD148 antibodies and antigen-binding regions thereof that bind to a human CD148 epitope, or substantially the same epitope, defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33. In another embodiment, the present invention provides an isolated antibody or antigen-binding region thereof that specifically binds to a human CD148 epitope, or substantially the same epitope, defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33. In another embodiment, the present invention provides a monoclonal antibody or antigen-binding region thereof that specifically binds to a human CD148 epitope, or substantially the same epitope, defined by one or more of the polypeptide sequences selected from the group consisting of amino acids 315-329, 318-332, 321-335, 324-338, 324-329, 324-332, 324-335, 447-725, 533-725, 715-973, 200-536, 533-725 and 200-725 of SEQ ID NO:33. Such antibodies or antigen-binding regions thereof can be prepared by any one of a number of processes disclosed below, for example, by immunizing an animal with at least a first CD148 antigenic composition and selecting from the immunized animal an antibody that substantially cross-reacts with the monoclonal antibodies of the present invention.

Antibodies with such combinations of properties can be readily identified by one or more or a combination of the receptor competition, ELISA, co-precipitation, and/or functional assays and the crossreactivity assays described herein.

The antibodies encompassed by the present invention include IgG, IgA, IgG1-4, IgE, IgM, and IgD antibodies, e.g., IgG1κ or IgG1λ isotypes, or IgG4κ or IgG4λ isotypes. In a particular embodiment, the antibody of the present invention is a IgG2 isotype. In one embodiment, human antibodies are produced in a non-human transgenic animal, e.g., a transgenic mouse, capable of producing multiple isotypes of human antibodies to CD148 (e.g., IgG, IgA and/or IgE) by undergoing V-D-J recombination and isotype switching. Accordingly, aspects of the invention include not only antibodies, antibody fragments, and pharmaceutical compositions thereof, but also non-human transgenic animals, B-cells, host cell transfectomas, and hybridomas which produce monoclonal antibodies. Methods of using the antibodies of the invention to detect a cell expressing CD148 or a related, cross-reactive growth factor receptor, or to inhibit growth, differentiation and/or motility of a cell expressing CD148, either in vitro or in vivo, are also encompassed by the invention. The present invention further encompasses pharmaceutical preparations containing the antibodies of the present invention, and methods of treating physiological disorders by administering the antibodies of the present invention.

The antibodies and antigen binding regions of the present invention can be constructed by any number of different methods, including, via immunization of animals (e.g., with an antigen that elicits the production of antibodies that specifically bind to and competitively inhibit the binding of at least one of an antibody of Ab-1 through Ab-8); via hybridomas (e.g., employing B-cells from transgenic or non-transgenic animals); via recombinant methods (e.g., CHO transfectomas; see, Morrison, S. (1985) Science 229:1202)), or, in vitro synthetic means (e.g., solid-phase polypeptide synthesis).

In some embodiments, the antibodies and antigen binding regions are human or humanized. Methods for humanizing non-human antibodies are well known in the art. Humanization can be essentially performed following the method of Winter and co-workers (Jones et al., Nature, 321:,522 (1986); Riechmann et al., Nature, 332: 323 (1988); Verhoeyen et al., Science, 239: 1534 (1988)). Briefly, human constant region genes are joined to appropriate human or non-human variable region genes. For example, the amino acid sequences which represent the antigen binding sites (CDRs, or complimentarily determining regions) of a parent murine monoclonal antibody are grafted at the DNA level onto human variable region framework sequences. The sequences of human constant regions genes may be found in Kabat et al. (1991) Sequences of Proteins of Immunological Interest, N.I.H. publication no. 91-3242. Human C region genes are readily available from known clones. The choice of antibody isotype will be guided by the desired effector functions, such as complement fixation, or activity in antibody-dependent cellular cytotoxicity. In certain embodiments, the isotype is $IgG_2$.

Human or humanized antibodies or antigen binding regions can also be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743.

Identification of suitable human antibody sequences may be facilitated by computer modeling. Modeling is well known in the art, and are used, for example, to avoid unnatural juxtaposition of non-human CDR regions with human variable framework regions, which can result in unnatural conformational restraints and concomitant loss of binding affinity. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

It is now possible to produce transgenic animals (e.g. mice) that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germline mutant mice will result in the production of human antibodies upon antigen challenge. See, e.g., Jakobovits et al., Proc. Natl. Acad. Sci USA, 90: 2551 (1993); Jakobovits et al., Nature, 362: 255 (1993); Bruggermann et al., Year in Immunol., 20 7: 33 (1993). Commercially accessible transgenic mice strains such as XenoMouse have been described; see, Green et al. Nature Genetics 7:13-21 (1994).

Recombinant methods for producing antibodies or antigen binding regions of the present invention begin with the isolated nucleic acid of desired regions of the immunoglobulin heavy and light chains such as those present in any of Ab-1 through Ab-8. Such regions can include, for example, all or part of the variable region of the heavy and light chains. Such regions can, in particular, include at least one of the CDRs of the heavy and/or light chains, and often, at least one CDR pair from from Ab-1 through Ab-8. A nucleic acid encoding an antibody or antigen binding region of the invention can be directly synthesized by methods of in vitro oligonucleotide synthesis known in the art. Alternatively, smaller fragments can be synthesized and joined to form a larger fragment using recombinant methods known in the art. Antibody binding regions, such as for Fab or F(ab')$_2$, may be prepared by cleavage of the intact protein, e.g. by protease or chemical cleavage. Alternatively, a truncated gene can be designed.

To express the antibodies or antigen binding regions thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational regulatory sequences. Nucleic acids encoding an antibody or antigen binding region of the invention can be cloned into a suitable expression vector and expressed in a suitable host. A suitable vector and host cell system can allow, for example, co-expression and assembly of the variable heavy and variable light chains of at least one of Ab-1 through Ab-8, or CDR containing polypeptides thereof. Suitable systems for expression can be determined by those skilled in the art.

Nucleic acids comprising polynucleotides of the present invention can be used in transfection of a suitable mammalian or nonmammalian host cells. In some embodiments, for expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most typical because such eukaryotic cells, and in particular mammalian cells, are more likely than prokaryotic cells to assemble and secrete a properly folded and immunologically active antibody or antigen binding region.

Expression vectors include plasmids, retroviruses, cosmids, YACs, EBV derived episomes, and the like. A convenient vector is one that encodes a functionally complete human CH (constrant heavy) or CL (constant light) immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions.

The expression vector and expression control sequences are chosen to be compatible with the expression host cell used. The antibody variable heavy chain nucleic acid and the antibody variable light chain nucleic acids of the present invention can be inserted into separate vectors or, frequently, both genes are inserted into the same expression vector. The nucleic acids can be inserted into the expression vector by standard methods (e.g., ligation of complementary restriction sites on the antibody nucleic acid fragment and vector, or blunt end ligation if no restriction sites are present). The heavy and light chain variable regions of Ab-1 through Ab-8, described herein, can be used to create full-length antibody genes of any antibody isotype by inserting them into expression vectors already encoding heavy chain constant and light chain constant regions of the desired isotype (and subclass) such that the VH segment is operatively linked to the CH segment(s) within the vector and the VL segment is operatively linked to the CL segment within the vector. Additionally or alternatively, the expression vector can encode a signal peptide that facilitates secretion of the antibody or antigen binding region chain from a host cell. The antibody or antigen binding region chain gene can be cloned into the vector such that the signal peptide is linked in-frame to the amino terminus of the antibody/antigen binding region chain gene. The signal peptide can be an immunoglobulin signal peptide or a heterologous signal peptide (i.e., a signal peptide from a non-immunoglobulin protein).

In addition to the CDR comprising sequence, the expression vectors of the invention carry regulatory sequences that control the expression of the sequence in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, and the like. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or beta-globin promoter.

In addition to the antibody or antigen binding region nucleic acids and regulatory sequences, the expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

Preferred mammalian host cells for expressing the recombinant antibodies or antigen binding regions of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells and SP2.0 cells. In particular for use with NS/0 myeloma cells, another preferred expression system is the GS gene expression system disclosed in WO 87/04462, WO 89/01036 and EP 338 841. When expression vectors of the invention are introduced into mammalian host cells, the antibodies or antigen binding regions are produced by culturing the host cells for a period of time sufficient to allow for expression of the antibody or antigen binding region in the host cells or, more preferably, secretion of the antibody or antigen binding region into the culture medium in which the host cells are grown.

Once expressed, antibodies and antigen binding regions of the invention can be purified according to standard methods in the art, including HPLC purification, fraction column chromatography, gel electrophoresis and the like (see, e.g., Scopes, Protein Purification, Springer-Verlag, NY, 1982). In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxylapatite chromatography; isoelectric focusing; polyacrylamide gel electrophoresis; and combinations of such and other techniques. In certain embodiments, a polypeptide is purified by fast protein liquid chromatography or by high pressure liquid chromotography (HPLC).

Generation of Hybridomas Producing Human Monoclonal Antibodies to CD148

Another aspect of the present invention includes a hybridoma cell that produces the antibody or antigen-binding region thereof of the present invention. A hybridoma cell may comprise a B cell obtained from a transgenic non-human animal having a genome comprising a human heavy chain transgene and a light chain transgene fused to an immortalized cell, wherein the hybridoma produces a detectable amount of the monoclonal antibody or antigen-binding region thereof of the present invention.

Mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells are cultured in medium in which the HAT is replaced with HT. Individual wells are then screened by ELISA for human anti-CD148 monoclonal IgM and IgG antibodies. Once extensive hybridoma growth occurs, medium is observed usually after 10-14 days. The antibody secreting hybridomas are replated, screened again, and if still positive for human IgG, anti-CD148 monoclonal antibodies, can be subcloned at least twice by limiting dilution. The stable subclones are then cultured in vitro to generate small amounts of antibody in tissue culture medium for characterization.

Generation of Transfectomas Producing Human Monoclonal Antibodies to CD148

Human antibodies of the invention can also be produced in a host cell transfectoma using, for example, a combination of recombinant DNA techniques and gene transfection methods as is well known in the art (Morrison, S. (1985) Science 229:1202). A transfectoma cell may comprise nucleic acids encoding a human heavy chain and a human light chain, wherein the transfectoma produces a detectable amount of the monoclonal antibody or antigen-binding region thereof of the present invention.

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or beta-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection). In a preferred embodiment of the present invention, the antibody chain genes and regulatory sequences are expressed in "split dhfr vectors" PDC323 and PDC324, as disclosed by Bianchi, A. A. and McGrew, J. T. (2003) "High-level expression of full antibodies using trans-complementing expression vectors," Bioengineering and Biotechnology, 84 (4): 439-444; and McGrew, J. T. and Bianchi, A. A. (2002) "Selection of cells expressing heteromeric proteins," U.S. patent application No. 20030082735, the contents of which are expressly incorporated herein by reference.

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells and SP2.0 cells. In particular for use with NS/0 myeloma cells, another preferred expression system is the GS gene expression system disclosed in WO 87/04462, WO 89/01036 and EP 338 841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by referenced for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences cab be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assemble into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCV products. These overlapping products are then combined by PCT amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric IgG1κ or IgG4κ antibodies. Similar plasmids can be constructed for expression of other heavy chain isotypes, or for expression of antibodies comprising lambda light chains.

Thus, in another aspect of the invention, the structural features of an human anti-CD148 antibodies of the invention are used to create structurally related human anti-CD148 antibodies that retain at least one functional property of the antibodies of the invention, such as binding to CD148. More specifically, one or more CDR regions of anti-CD148 antibodies can be combined recombinantly with known human framework regions and CDRs to create additional, recombinantly-engineered, human anti-CD148 antibodies of the invention.

Accordingly, anti-CD148 antibodies of the present invention can be used to prepare an anti-CD148 antibody by preparing an anti-CD148 antibody comprising (1) human heavy chain framework regions and human heavy chain CDRs; and (2) human light chain framework regions and human light chain CDRs, wherein the antibody retains the ability to bind to CD148.

The ability of the antibody to bind CD148 can be determined using standard binding assays (e.g., an ELISA). Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of anti-CD148 antibodies. The antibodies further can comprise the CDR2s of anti-CD148 antibodies. The antibodies further can comprise the CDR1s of anti-CD148 antibodies. Accordingly, the invention further provides anti-CD148 antibodies comprising: (1) human heavy chain framework regions, a human heavy chain CDR1 region, a human heavy chain CDR2 region, and a human heavy chain CDR3 region, wherein the human heavy chain CDR3 region is the CDR3 of anti-CD148 antibodies; and (2) human light chain framework regions, a human light chain CDR1 region, a human light chain CDR2 region, and a human light chain CDR3 region, wherein the human light chain CDR3 region is the CDR3 of anti-CD148 antibodies, wherein the antibody binds CD148. The antibody may further comprise the heavy chain CDR2 and/or the light chain CDR2 of anti-CD148 antibodies. The antibody may further comprise the heavy chain CDR1 and/or the light chain CDR1 of anti-CD148 antibodies.

Preferably, the CDR1, 2, and/or 3 of the engineered antibodies described above comprise the exact amino acid sequence(s) as those of anti-CD148 antibodies disclosed herein. However, the ordinarily skilled artisan will appreciate that some deviation from the exact CDR sequences may be possible while still retaining the ability of the antibody to bind CD148 effectively (e.g., conservative substitutions). Accordingly, in another embodiment, the engineered antibody may be composed of one or more CDRs that are, for example, 90%, 95%, 98% or 99.5% identical to one or more CDRs of anti-CD148 antibodies.

Characterization of Binding of Human Monoclonal Antibodies to CD148

To characterize binding of anti-human CD148 human monoclonal antibodies of the invention, sera from immunized mice can be tested, for example, by ELISA. Briefly, microtiter plates are coated with purified CD148 at 0.25 μg/ml in PBS, and then blocked with 5% bovine serum albumin in PBS. Dilutions of plasma from CD148-immunized mice are added to each well and incubated for 1-2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with CD148 antigen. Hybridomas that bind with high affinity to CD148 will be subcloned and further characterized. One clone from each hybridoma, which retains the reactivity of the parent cells (by ELISA), can be chosen for making a 5-10 vial cell bank stored at −140° C., and for antibody purification.

To purify human anti-CD148 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-CD148 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD148 coated-ELISA plates as described above. Biotinylated MAb binding can be detected with a strep-avidin-alkaline phosphatase probe.

To determine the isotype of purified antibodies, isotype ELISAs can be performed. Wells of microtiter plates can be coated with 10 g/ml of anti-human Ig overnight at 4° C. After blocking with 5% BSA, the plates are reacted with 10 g/ml of monoclonal antibodies or purified isotype controls, at ambient temperature for two hours. The wells can then be reacted with either human IgG1 or human IgM-specific alkaline phosphatase-conjugated probes. Plates are developed and analyzed as described above.

In order to demonstrate binding of monoclonal antibodies to live cells expressing the CD148, flow cytometry can be used. Briefly, cell lines expressing CD148 (grown under standard growth conditions) are mixed with various concentrations of monoclonal antibodies in PBS containing 0.1% Tween 80 and 20% mouse serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD148 human IgGs can be further tested for reactivity with CD148 antigen by Western blotting. Briefly, cell extracts from cells expressing CD148 can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Transgenic Nonhuman Animals Which Generate Human Monoclonal Anti-CD148 Antibodies Human monoclonal antibodies directed against CD148 polypeptides can be generated using transgenic mice carrying parts of the human immune system rather than the mouse system. These transgenic mice, referred to herein as "HuMAb" mice, contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, et al. (1994) Nature 368(6474): 856-859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). The preparation of HuMAb mice is described in detail below and in Taylor, L. et al (1992) Nucleic Acids Research 20:6287-6295; Chen, J. et al. (1993) International Immunology 5: 647-656; Tuaillon et al. (1993) Proc. Natl. Acad. Sci USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Lonberg et al., (1994) Nature 368(6474): 856-859; Lonberg, N. (1994) Handbook of Experimental Pharmacology 113:49-101; Taylor, L. et al. (1994) International Immunology 6: 579-591; Lonberg, N. and Huszar, D. (1995) Intern. Rev. Immunol. Vol. 13: 65-93; Harding, F. and Lonberg, N. (1995) Ann. N.Y. Acad. Sci 764:536-546; Fishwild, D. et al. (1996) Nature Biotechnology 14: 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992, the disclosures of all of which are hereby incorporated by reference in their entity. Alternatively, transgenic mice can be used to generate human anti-CD148 antibodies.

To generate fully human monoclonal antibodies to CD148, HuMAb mice can be immunized with a purified or enriched preparation of CD148 antigen and/or cells expressing CD148, as described by Lonberg, N. et al. (1994) Nature 368(6474): 856-859; Fishwild, D. et al. (1996) Nature Biotechnology 14: 845-851 and WO 98/24884. Preferably, the mice will be 6-16 weeks of age upon the first infusion. For example, a purified or enriched preparation (5-20 µg) of CD148 antigen (e.g., purified from CD148-expressing LNCaP cells) can be used to immunize the HuMAb mice intraperitoneally. In the event that immunizations using a purified or enriched preparation of CD148 antigen do not result in antibodies, mice can also be immunized with cells expressing CD148, e.g., a tumor cell line, to promote immune responses.

Cumulative experience with various antigens has shown that the HuMAb transgenic mice respond well when initially immunized intraperitoneally (IP) with antigen in complete Freund's adjuvant, followed by every other week i.p. immunizations (up to a total of 6) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-CD148 human immunoglobulin can be used for fusions. Mice can be boosted intravenously with antigen 3 days before sacrifice and removal of the spleen. It is expected that 2-3 fusions for each antigen may need to be performed. Several mice will be immunized for each antigen. For example, a total of twelve HuMAb mice of the HC07 and HC012 strains can be immunized.

In yet another aspect, the invention provides transgenic non-human animals, e.g., a transgenic mice, which are capable of expressing human monoclonal antibodies that specifically bind to CD148 epitopes of the present invention. In a preferred embodiment, the transgenic non-human animals, e.g., the transgenic mice (HuMAb mice), have a genome comprising a human heavy chain transgene and a light chain transgene. In one embodiment, the transgenic non-human animals, e.g., the transgenic mice, have been immunized with a purified or enriched preparation of CD148 antigen and/or cells expressing CD148. Preferably, the transgenic non-human animals, e.g., the transgenic mice, are capable of producing multiple isotypes of human monoclonal antibodies to CD148 (e.g., IgG, IgA and/or IgE) by undergoing V-D-J recombination and isotype switching. Isotype switching may occur by, e.g., classical or non-classical isotype switching.

The design of a transgenic non-human animal that responds to foreign antigen stimulation with a heterologous antibody repertoire, requires that the heterologous immunoglobulin transgenes contain within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, Fundamental Immunology, 2nd edition (1989), Paul William E., ed. Raven Press, N.Y., which is incorporated herein by reference.

In certain embodiments, the transgenic non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., Nucl. Acids Res. 15:7305-7316 (1991); Sideras et al., Intl. Immunol. 1:631-642 (1989), which are incorporated herein by reference). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. The transgene may, for example, be constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to CD148 antigen.

Transgenes may also comprise an unrearranged "minilocus." Such transgenes typically comprise a substantial portion of the C, D, and J segments as well as a subset of the V gene segments. In such transgene constructs, the various regulatory sequences, e.g., promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

Transgenic animals may also be used to generate human antibodies to CD148 containing at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the JH deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human kappa light chain construct (described in Example 14 of WO 98/24884), and a deletion at each endogenous mouse heavy chain locus that removes all of the functional JH segments (described in Example 10 of WO 98/24884). Such animals are bred with mice that are homozygous for the deletion of the JH segments (Examples 10 of WO 98/24884) to produce offspring that are homozygous for the JH deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the JH region introduced as described in Example 9 and 12 of WO 98/24884. Furthermore, a substantial fraction of the B cells will be monospecific with regards to the human or mouse light chains because expression of the single copy of the rearranged human kappa light chain gene will allelically and isotypically exclude the rearrangement of the endogenous mouse kappa and lambda chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, preferably 40 to 80% of the spleen and lymph node B cells express exclusively human IgG protein. The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., *staphylococcus* protein A. Typically, the immunoglobulins will exhibit an affinity for preselected antigens of at least about $10^7$ M$^{-1}$, preferably at least about $10^9$ M$^{-1}$, more preferably at least about $10^{10}$ M$^{-1}$, $10^{11}$ M$^{-1}$, $10^{12}$ M$^{-1}$, or greater, e.g., up to $10^{13}$ M$^{-1}$ or greater.

In some embodiments, it may be preferable to generate mice with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g., by hybridization or DNA sequencing, as being from a species of organism other than the transgenic animal.

The transgenic mice of the present invention can be immunized with a purified or enriched preparation of CD148 antigen and/or cells expressing CD148 as described previously. The mice will produce B cells which undergo class-switching via intratransgene switch recombination (cis-switching) and express immunoglobulins reactive with CD148. The immunoglobulins can be human sequence antibodies, wherein the heavy and light chain polypeptides are encoded by human transgene sequences, which may include sequences derived by somatic mutation and V region recombinatorial joints, as well as germline-encoded sequences; these human sequence immunoglobulins can be referred to as being substantially identical to a polypeptide sequence encoded by a human $V_L$ or $V_H$ gene segment and a human $J_L$ or $J_L$ segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRS, or in regions where somatic mutations are known to cluster.

The human sequence antibodies which bind to the predetermined antigen can result from isotype switching, such that human antibodies comprising a human sequence γ chain (such as γ1, γ2a, γ2B, or γ3) and a human sequence light chain (such as the kappa light chain) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast in no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$ gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which include (1) transgenic animals containing an unrearranged heavy and rearranged light immunoglobulin transgene; (2) transgenic animals containing an unrearranged heavy and unrearranged light immunoglobulin transgene; (3) transgenic animals containing rearranged heavy and an unrearranged light immunoglobulin transgene; and (4) transgenic animals containing rearranged heavy and rearranged light immunoglobulin transgenes.

Bispecific/Multispecific Molecules which Bind to CD148

In yet another embodiment of the invention, human monoclonal antibodies to CD148, or antigen-binding regions thereof, can be derivatized or linked to another functional molecule, e.g., another peptide or protein (e.g., an Fab' fragment) to generate a bispecific or multispecific molecule which binds to multiple binding sites or target epitopes. For example, an antibody or antigen-binding region of the invention can be functionally linked (e.g., by chemical coupling, genetic fusion, noncovalent association or otherwise) to one or more other binding molecules, such as another antibody, antibody fragment, peptide or binding mimetic.

Accordingly, the present invention includes bispecific and multispecific molecules comprising at least one first binding specificity for CD148 and a second binding specificity for a second target epitope. In a particular embodiment of the invention, the second target epitope is an Fc receptor, e.g., human FcγRI (CD64) or a human Fcα receptor (CD89). Therefore, the invention includes bispecific and multispecific molecules capable of binding both to FcγR, FcαR or FcεCR expressing effector cells (e.g., monocytes, macrophages or polymorphonuclear cells (PMNs)), and to target cells expressing CD148. These bispecific and multispecific molecules target CD148 expressing cells to effector cell and, like the human monoclonal antibodies of the invention, trigger Fc receptor-mediated effector cell activities, such as phagocytosis of a CD148 expressing cells, antibody dependent cell-mediated cytotoxicity (ADCC), cytokine release, or generation of superoxide anion.

Bispecific and multispecific molecules of the invention can further include a third binding specificity, in addition to an anti-Fc binding specificity and an anti-CD148 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In another embodiment, bispecific and multispecific molecules of the invention comprise a binding specificity for an FcαR or an FcγR present on the surface of an effector cell, and a second binding specificity for a target cell antigen, e.g., CD148.

In another embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of these preferred monoclonal antibodies are described by Fanger et al. in PCT application WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are MAb 22, MAb 32, MAb 44, MAb 62 and MAb 197. The hybridoma producing MAb 32 is available from the American Type Culture Collection, ATCC Accession No. HB9469. Anti-FcγRI MAb 22, F(ab')$_2$ fragments of MAb 22, and can be obtained from Medarex, Inc. (Annandale, N.J.). In other embodiments, the anti-Fcγ receptor antibody is a humanized form of monoclonal antibody 22 (H22). The production and characterization of the H22 antibody is described in Graziano, R. F. et al. (1995) J. Immunol 155 (10): 4996-5002 and PCT/US93/10384. The H22 antibody producing cell line was deposited at the American Type Culture Collection on Nov. 4, 1992 under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity (approximately equal to $5\times10^7$ M$^{-1}$) for both IgA1 and IgA2, which is increased upon exposure to cytokines such as G-CSF or GM-CSF (Morton et al., Critical Reviews in Immunology 16:423-440 (1996)). Four FcαRI-specific monoclonal antibodies, identified as A3, A59, A62 and A77, which bind FcαRI outside the IgA ligand binding domain, have been described, for example, by Monteiro et al., J. Immunol. 148:1764 (1992).

In another embodiment, the antibodies of the present invention may take the form of a scFv fragment fused directly to the Fc portion (CH2 & CH3) of the human IgG1 isotpye (referred to herein as a scFv-Fc construct). Construction of scFv-Fc fusions are disclosed, for example, by Fredericks et al., Protein Engineering Design and Selection 17:95-106 (2003), Powers et al., J. Imunological Methods 251:123-135 (2001), Shu et al., PNAS 90:7995-7999 (1993), and Hayden et al., Therapeutic Immunology 1:3-15 (1994).

FcαRI and FcγRI are preferred trigger receptors for use in the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

In other embodiments, bispecific and multispecific molecules of the invention further comprise a binding specificity which recognizes, e.g., binds to, a target cell antigen, e.g., CD148. In one particular embodiment, the binding specificity is provided by a human monoclonal antibody of the present invention.

While human monoclonal antibodies are preferred, other antibodies which can be employed in the bispecific or multispecific molecules of the invention are murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., Science 240:1041-1043 (1988); Liu et al., PNAS 84:3439-3443 (1987); Liu et al., 1987, J. Immunol. 139:3521-3526; Sun et al. (1987) PNAS 84:214-218; Nishimura et al., Canc. Res.

47:999-1005 (1987); Wood et al., Nature 314:446-449 (1985); and Shaw et al., J. Natl Cancer Inst. 80:1553-1559 (1988).

The chimeric antibody can be further humanized by replacing sequences of the Fv variable region which are not directly involved in antigen binding with equivalent sequences from human Fv variable regions. General reviews of humanized chimeric antibodies are provided by Morrison, Science 229: 1202-1207 (1985) and by Oi et al., BioTechniques 4:214 (1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al., Nature 321:552-525 (1986); Verhoeyan et al., Science 239:1534 (1988); and Beidler et al., J. Immunol. 141:4053-4060 (1988).

The CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, Humanized Antibodies to Fc Receptors for Immunoglobulin G on Human Mononuclear Phagocytes.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcγR and triggers at least one effector function.

Bispecific and multispecific molecules of the present invention can be made using chemical techniques (see e.g., D. M. Kranz et al., Proc. Natl. Acad. Sci. USA 78:5807 (1981), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-CD148 binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.).

Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. One or more of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly (Gly).sub.5, (Gly).sub.8), poly(Gly-Ala), and polyalanines. Combinations of Gly and Ala are also preferred.

Non-peptide linkers are also possible. For example, alkyl linkers such as —NH— (CH.sub.2)s-C(O)—, wherein s=2-20 can be used. These alkyl linkers may further be substituted by any non-sterically hindering group such as lower alkyl (e.g., C1-C6) lower acyl, halogen (e.g., Cl, Br), CN, NH$_2$, phenyl, etc. An exemplary non-peptide linker is a PEG linker, and has a molecular weight of 100 to 5000 kDa, preferably 100 to 500 kDa. The peptide linkers may be altered to form derivatives in the same manner as described above.

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a MabxMAb, MabxFab, Fabx F(ab')$_2$ or ligandxFab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multspecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

In the antibodies and antigen-binding regions thereof may also be combined with a vehicle for targeted delivery to a specified location.

In one embodiment, this invention provides antibodies, or antigen-binding regions thereof, that are attached to at least one vehicle (F1, F2) through the N-terminus, C-terminus or a side chain of one of the amino acid residues of the peptide(s). Multiple vehicles may also be used; e.g., Fc's at each terminus or an Fc at a terminus and a PEG group at the other terminus or a side chain.

An Fc domain is one preferred vehicle. The Fc domain may be fused to the N or C termini of the peptides or at both the N and C termini.

As noted above, Fc variants are suitable vehicles within the scope of this invention. A native Fc may be extensively modified to form an Fc variant in accordance with this invention, provided binding to the salvage receptor is maintained. See, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.
2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionyl residue, especially when the molecule is expressed recombinantly in a bacterial cell such as *E. coli*.
3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.
4. One or more glycosylation sites are removed. Residues that are typically glycosylated (e.g., asparagine) may confer cytolytic response. Such residues may be deleted or substituted with unglycosylated residues (e.g., alanine).
5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.
6. Sites are removed that affect binding to Fc receptors other than a salvage receptor. A native Fc may have sites for interaction with certain white blood cells that are not required for the fusion molecules of the present invention and so may be removed.
7. The ADCC site is removed. ADCC sites are known in the art. See, for example, Molec. Immunol. 29 (5):633-9 (1992) with regard to ADCC sites in IgG1. These sites, as well, are not required for the fusion molecules of the present invention and so may be removed.
8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used for F1 and F2. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kDa") to about 100 kDa, more preferably from about 5 kDa to about 50 kDa, most preferably from about 5 kDa to about 10 kDa. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis as known in the art. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by al-6 linkages. The dextran itself is available in many molecular weight ranges, and is readily available in molecular weights from about 1 kDa to about 70 kDa. Dextran is a suitable water-soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kDa to about 20 kDa is preferred when dextran is used as a vehicle in accordance with the present invention.

Antibody Conjugates/Immunotoxins

In another aspect, the present invention features a human anti-CD148 monoclonal antibody, or a fragment thereof, conjugated to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be conjugated to an antibody of the invention include calicheamicin and duocarmycin. An antibody of the present invention can be conjugated to a radioisotope, e.g., radioactive iodine, to generate cytotoxic radiopharmaceuticals for treating a CD148-related disorder, such as a cancer.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Pharmaceutical Compositions

Pharmaceutical compositions of anti-CD148 antibodies are within the scope of the present invention. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount of an antibody, or a fragment, variant, derivative or fusion thereof as described herein, in admixture with a pharmaceutically acceptable carrier and/or a pharmaceutically acceptable salt. In a preferred embodiment, pharmaceutical compositions comprise antibodies that bind CD148 epitopes that activate CD148 actrivity in admixture with a pharmaceutically acceptable carrier and/or a pharmaceutically acceptable salt. Typically, the specific binding agents will be sufficiently purified for administration to an animal.

Pharmaceutically Acceptable Carriers

As used herein, "pharmaceutically acceptable carrier" includes any and all solvents, dispersion media, coatings, antibacterial and antifungal agents, isotonic and absorption delaying agents, and the like that are physiologically compatible. In particular embodiments, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound. In another particular embodiment, the pharmaceutical compositions are formulated with a carrier that is pharmaceutically acceptable in humans.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamin-e, N-methylglucamine, chloroprocaine, choline, diethanolamine, ethylenediamine, procaine and the like.

The pharmaceutical compositions of the present invention may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific antibody.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier. By way of example, the pharmaceutical compositions of the present invention may contain an anti-CD148 antibody or antigen-binding region thereof in a concentration of from about 1 mg/ml to about 30 mg/ml, or alternatively from about 5 mg/ml to about 30 mg/ml.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

Therapeutically Effective Dosages

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. A "therapeutically effective dosage" preferably inhibits tumor growth by at least about 20%, more preferably by at least about 40%, even more preferably by at least about 60%, and still more preferably by at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the antibody or antigen-binding region is being used, the route of administration, and the size (body weight, body surface or organ size) and condition (the age and general health) of the patient. Accordingly, the clinician may titer the dosage and modify the route of administration to obtain the optimal therapeutic effect.

A preferred anti-CD148 antibody or antigen-binding region thereof has the ability to substantially bind to CD148 in solution at concentrations of less than 1 uM, preferably less than 0.1 uM, and more preferably less than 0.01 uM. By "substantially" is meant that at least a 50 percent reduction in endothelial cell proliferation and migration is observed by modulation in the presence of the an anti-CD148 antibody or antigen-binding region thereof, and at 50% reduction is referred to herein as an IC50 value.

A therapeutically effective amount of an anti-CD148 antibody or antigen-binding region thereof of this invention is typically an amount such that when administered in a physiologically tolerable composition is sufficient to achieve a plasma concentration (based on cmax data after a single dose of antibody) of, for example, from about 0.01 ug/ml to about 300 ug/ml. In another embodiment, the concentration may be from about 1 ug/ml to about 300 ug/ml. In yet another embodiment, the concentration may be from about 1 ug/ml to about 75 ug/ml. In yet another embodiment, the concentration may be from about 15 ug/ml to about 50 ug/ml. Dosages may, of course, vary according to frequency and duration of administration.

A therapeutically effective amount of an anti-CD148 antibody or antigen-binding region thereof of this invention in the form of a polypeptide is typically an amount of polypeptide such that when administered in a physiologically tolerable composition is sufficient to achieve a plasma concentration of from about 0.001 ug/ml to about 10 ug/ml, or from about 0.05 ug/ml to about 1.0 ug/ml. Based on a polypeptide having a mass of about 15,000 grams per mole (i.e. 15,000 Da), the plasma concentration in molarity may be, for example, from about 0.0001 uM to about 1 mM. Stated differently, the dosage per body weight can vary from about 0.01 mg/kg to about 30 mg/kg, or from about 0.05 mg/kg to about 20 mg/kg, in one or more dose administrations daily, for one or several days. A typical dosage may range from about 0.1 mg/kg to up to about 100 mg/kg or more, depending on the factors mentioned above. In other embodiments, the dosage may range from 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Methods of administering the compositions (e.g., human antibodies, multispecific and bispecific molecules) of the invention are known in the art. Suitable dosages of the molecules used will depend on the age and weight of the subject and the particular drug used. The molecules can be coupled to radionuclides, such as 131I, 90Y, 105Rh, indium-111, etc., as described in Goldenberg, D. M. et al. (1981) Cancer Res. 41: 4354-4360, and in EP 0365 997. In another aspect the invention relates to an immunoconjugate comprising an antibody according to the invention linked to a radioisotope, cytotoxic agent (e.g., calicheamicin and duocarmycin), a cytostatic agent, or a chemotherapeutic drug. The compositions (e.g., human antibodies, multispecific and bispecific molecules) of the invention can also be coupled to anti-infectious agents.

Routes of Administration

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent of the present invention such as an antibody or antigen-binding region thereof can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

When parenteral administration is contemplated, the therapeutic compositions for use in this invention may be in the form of a pyrogen-free, parenterally acceptable aqueous solution comprising the desired specific binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. In one embodiment of the present invention, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate [Sidman et al., Biopolymers, 22:547-556 (1983)], poly (2-hydroxyethyl-methacrylate) [Langer et al., J. Biomed. Mater. Res., 15:167-277, (1981)] and [Langer et al., Chem. Tech., 12:98-105(1982)], ethylene vinyl acetate (Langer et al., supra) or poly-D(-)-3-hydroxybutyric acid (EP 133,988). Sustained-release compositions also include liposomes, which can be prepared by any of several methods known in the art. See e.g., Eppstein et al., Proc. Natl. Acad. Sci. (USA), 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

Combination Therapies

In another aspect, the present invention provides a composition, e.g., a pharmaceutical composition, containing one or a combination of human antibodies, or antigen-binding region(s) thereof, of the present invention, formulated together with a pharmaceutically acceptable carrier. In another embodiment, the compositions include a combination of multiple (e.g., two or more) isolated human antibodies or antigen-binding regions thereof of the invention. In a more particular embodiment, each of the antibodies or antigen-binding regions thereof of the composition binds to a distinct, pre-selected epitope of CD148.

In one embodiment, human anti-CD148 monoclonal antibodies having complementary activities are used in combination, e.g., as a pharmaceutical composition, comprising two or more human anti-CD148 monoclonal antibodies. For example, a human monoclonal antibody that inhibits angiogenesis or the growth of cells expressing CD148, may also be combined with another human antibody that mediates highly effective killing of target cells in the presence of effector cells.

In another embodiment, the composition comprises one or a combination of bispecific or multispecific molecules of the invention (e.g., which contains at least one binding specificity for an Fc receptor and at least one binding specificity for CD148).

The invention thus includes administration of the antibodies or antigen-binding regions thereof of the present invention administered to the same patient in combination with one or more additionally suitable agent(s), each being administered according to a regimen suitable for that medicament. This includes concurrent administration of a specific binding agent of the invention and one or more suitable agents. As used herein, the terms "concurrently administered" and "concurrent administration" encompass substantially simultaneous administration of one or more antibody according to the invention and one or more additionally suitable agents(s).

As used herein, the term, "non-concurrent" administration encompasses administering one or more antibodies or antigen-binding regions thereof according to the invention and one or more additionally suitable agent(s), at different times, in any order, whether overlapping or not. This includes, but is not limited to, sequential treatment (such as pretreatment, post-treatment, or overlapping treatment) with the components of the combination, as well as regimens in which the drugs are alternated, or wherein one component is administered long-term and the other(s) are administered intermittently. Components may be administered in the same or in separate compositions, and by the same or different routes of administration.

Combination therapy with growth factors can include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF0, TNF1, TNF2, G-CSF, Meg-CSF, GM-CSF, thrombopoietin, stem cell factor, and erythropoietin. Other are compositions can include known angiopoietins, for example Ang-1, -2, -4, —Y, and/or the human Ang-like polypeptide, and/or vascular endothelial growth factor (VEGF). Growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor-1, glial cell line-derived neutrophic factor receptor-2, growth related protein, growth related protein-1, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-1, transforming growth factor-1.2, transforming growth factor-2, transforming growth factor-3, transforming growth factor-5, latent transforming growth factor-1, transforming growth factor-I binding protein I, transforming growth factor-I binding protein II, transforming growth factor-I binding protein III, tumor necrosis factor receptor type I (TNF-R1), tumor necrosis factor receptor type II (TNF-R2), urokinase-type plasminogen activator receptor, vascular endothelial growth factor, and chimeric proteins and biologically or immunologically active fragments thereof.

It will be appreciated that the antibodies or antigen-binding regions thereof of the invention may be administered with one or more anti-inflammatory agents. As used herein, the term "anti-inflammatory agent" refers generally to any agent that reduces inflammation or swelling in a patient. A number of exemplary anti-inflammatory agents are recited herein, but it will be appreciated that there may be additional suitable anti-inflammatory agents not specifically recited herein, but which are encompassed by the present invention.

The anti-inflammatory agent can be, for example, a compound that inhibits the interaction of inflammatory cytokines with their receptors. Examples of cytokine inhibitors useful in combination with the specific binding agents of the invention include, for example, antagonists (such as antibodies) of TGF-beta, as well as antagonists (such as antibodies) directed against interleukins involved in inflammation. Such interleukins are described herein and preferably include, but are not limited to, IL-1, IL-2, IL-3, IL-4, IL-5, IL-6, IL-8, IL-9, IL-1 I, IL-12, IL-13, IL-17, and IL-18. See Feghali, et al., Frontiers in Biosci., 2:12-26 (1997). Exemplary antibody antagonists also include antibodies directed against the 21-28 kD cell surface glycoprotein CD52 (such as CamPath®, Berlex Laboratories), IL-8 (and anti-IL8-RB antibodies), B-FGF (and anti-B-FGF receptor antibodies), anti-TWEAK antibodies (and anti-TWEAK receptor (i.e., TWEAKR) antibodies), anti-Adam/Disintegrin antibodies, anti-eph receptor, anti-ephrin antibodies, and anti-PDGF-BB antibodies.

Specific antibodies or antigen-binding regions thereof of the invention also may be administered in combination with inhibitors of Protein Kinase A Type 1 to enhance T cell proliferation in HIV-infected patients who are receiving antiretroviral therapy.

Nerve growth factors (NGFs) also can be combined with the antibodies or antigen-binding regions thereof of the invention to treat certain conditions. Such conditions include neurodegenerative diseases, spinal cord injury and multiple sclerosis. Other conditions treatable with this combination are glaucoma and diabetes.

A preferred combination therapy relates to antibodies or antigen-binding regions thereof of the invention administered to a patient in combination with one or more suitable 1L-1 inhibitor. Inhibitors of IL-1 include, but are not limited to, receptor-binding peptide fragments of IL-1, antibodies directed against IL-1 or IL-1 beta or IL-1 receptor type I, and recombinant proteins comprising all or portions of receptors for IL-1 or modified variants thereof, including genetically-modified muteins, multimeric forms and sustained-release formulations. Specific antagonists include IL-Ira polypeptides, IL-1 beta converting enzyme (ICE) inhibitors, antagonistic type I IL-1 receptor antibodies, IL-1 binding forms of type I IL-1 receptor and type II IL-1 receptor, antibodies to IL-1, including IL-1 alpha and IL-1 beta and other IL-1 family members, and a therapeutic known as IL-1 Trap (Regeneron). IL-Ira polypeptides include the forms of IL-Ira described in U.S. Pat. No. 5,075,222 and modified forms and variants including those described in U.S. Pat. No. 5,922,573, WO 91/17184, WO 92 16221, and WO 96 09323. IL-1 beta converting enzyme (ICE) inhibitors include peptidyl and small molecule ICE inhibitors including those described in PCT patent applications WO 91/15577; WO 93/05071; WO 93/09135; WO 93/14777 and WO 93/16710; and European patent application 0 547 699. Non-peptidyl compounds include those described in PCT patent application WO 95/26958, U.S. Pat. No. 5,552,400, U.S. Pat. No. 6,121,266, and Dolle et al., J. Med. Chem., 39, pp. 2438-2440 (1996). Additional ICE inhibitors are described in U.S. Pat. Nos. 6,162,790, 6,204,261, 6,136,787, 6,103,711, 6,025,147, 6,008,217, 5,973,111, 5,874,424, 5,847,135, 5,843,904, 5,756,466, 5,656,627, 5,716,929. IL-1 binding forms of Type I IL-1 receptor and type II IL-1 receptor are described in U.S. Pat. Nos. 4,968,607, 4,968,607, 5,081,228, U.S. Pat. No. Re 35,450, U.S. Pat. No. 5,319,071, and 5,350,683. Other suitable IL-1 antagonists include, but are not limited to, peptides derived from IL-1 that are capable of binding competitively to the IL-1 signaling receptor, IL-1 R type I. Additional guidance regarding certain IL-1 (and other cytokine) antagonists can be found in U.S. Pat. No. 6,472,179.

Additionally, TNF inhibitors are suitable, and include, but are not limited to, receptor-binding peptide fragments of TNF-alpha, antisense oligonucleotides or ribozymes that inhibit TNF.alpha. production, antibodies directed against TNF-alpha, and recombinant proteins comprising all or portions of receptors for TNF-alpha or modified variants thereof, including genetically-modified muteins, multimeric forms and sustained-release formulations. Also suitable are TACE (Tumor Necrosis Factor-alpha Converting Enzyme) inhibitors, such as TAPI (Immunex Corp.) and GW-3333X (Glaxo Wellcome Inc.). Also suitable are molecules that inhibit the formation of the IgA-alpha-1AT complex, such as the peptides disclosed in EP 0 614 464 B, or antibodies against this complex. Additionally suitable molecules include, but are not limited to, TNF-alpha-inhibiting disaccharides, sulfated derivatives of glucosamine, or other similar carbohydrates described in U.S. Pat. No. 6,020,323. Further suitable molecules include peptide TNF-alpha inhibitors disclosed in U.S. Pat. Nos. 5,641,751 and 5,519,000, and the D-amino acid-containing peptides described in U.S. Pat. No. 5,753,628. In addition, inhibitors of TNF-alpha converting enzyme are also suitable. WO 01/03719 describes further additional agents which can be used in combination in accordance with the invention.

Still Further suitable compounds include, but are not limited to, small molecules such as thalidomide or thalidomide analogs, pentoxifylline, or matrix metalloproteinase (MMP) inhibitors or other small molecules. Suitable MMP inhibitors for this purpose include, for example, those described in U.S. Pat. Nos. 5,883,131, 5,863,949 and 5,861,510 as well as mercapto alkyl peptidyl compounds as described in U.S. Pat. No. 5,872,146. Other small molecules capable of reducing TNF-alpha production, include, for example, the molecules described in U.S. Pat. Nos. 5,508,300, 5,596,013, and 5,563,143. Additional suitable small molecules include, but are not limited to, MMP inhibitors as described in U.S. Pat. Nos. 5,747,514, and 5,691,382, as well as hydroxamic acid derivatives such as those described in U.S. Pat. No. 5,821,262. Further suitable molecules include, for example, small molecules that inhibit phosphodiesterase IV and TNF-alpha production, such as substituted oxime derivatives (WO 96/00215), quinoline sulfonamides (U.S. Pat. No. 5,834,485), aryl furan derivatives (WO 99/18095) and heterobicyclic derivatives (WO 96/01825; GB 2 291 422 A). Also useful are thiazole derivatives that suppress TNF-alpha and IFN-gamma (WO 99/15524), as well as xanthine derivatives that suppress TNF-alpha and other proinflammatory cytokines (see, for example, U.S. Pat. Nos. 5,118,500, 5,096,906 and 5,196,430). Additional small molecules useful for treating the hereindescribed conditions include those disclosed in U.S. Pat. No. 5,547,979.

Further examples of drugs and drug types which can be administered by combination therapy include, but are not limited to, antivirals, antibiotics, analgesics (e.g., acetaminophen, codeine, propoxyphene napsylate, oxycodone hydrochloride, hydrocodone bitartrate, tramadol), corticosteroids, antagonists of inflammatory cytokines, Disease-Modifying Anti-Rheumatic Drugs (DMARDs), Non-Steroidal Anti-Inflammatory drugs (NSAIDs), and Slow-Acting Anti-Rheumatic Drugs (SAARDs).

Exemplary Disease-Modifying Anti-Rheumatic Drugs (DMARDs) include, but are not limited to: Rheumatrex™ (methotrexate); Enbrel® (etanercept); Remicade® (infliximab); Humira™ (adalimumab); Segard® afelimomab); Arava™ (leflunomide); Kineret™ (anakinra); Arava™ (leflunomide); D-penicillamine; Myochrysine; Plaquenil; Ridaura™ (auranofin); Solganal; lenercept (Hoffman-La Roche); CDP870 (Celltech); CDP571 (Celltech), as well as the antibodies described in EP 0 516 785 B1, U.S. Pat. No. 5,656,272, EP 0 492 448 A1; onercept (Serono; CAS reg. no. 199685-57-9); MRA (Chugai); Imuran™ (azathioprine); NFKB inhibitors; Cytoxan™ (cyclophosphamide); cyclosporine; hydroxychloroquine sulfate; minocycline; sulfasalazine; and gold compounds such as oral gold, gold sodium thiomalate and aurothioglucose.

Further suitable molecules include, for example, soluble TNFRs derived from the extracellular regions of TNF-alpha receptor molecules other than the p55 and p75 TNFRs, such as for example the TNFR described in WO 99/04001, including TNFR-Ig's derived from this TNFR. Additional suitable TNF-alpha inhibitors are suitable for use as described herein. These include the use not only of an antibody against TNF-alpha or TNFR as described herein, but also a TNF-alpha derived peptide that can act as a competitive inhibitor of TNF-alpha (such as those described in U.S. Pat. No. 5,795,859 or U.S. Pat. No. 6,107,273), TNFR-IgG fusion proteins, such as one containing the extracellular portion of the p55 TNF-alpha receptor, a soluble TNFR other than an IgG fusion protein, or other molecules that reduce eridogenous TNF-alpha levels, such as inhibitors of the TNF-alpha converting enzyme (see e.g., U.S. Pat. No. 5,594,106), or small molecules or TNF-alpha inhibitors, a number of which are described herein.

With respect to antibodies to TNF, although dose will optimally be determined by an experienced healthcare provider in accordance with the specific needs of the patient in mind, one exemplary preferred dose range for an antibody against TNF-alpha is 0.1 to 20 mg/kg, and more preferably is 1-10 mg/kg. Another preferred dose range for anti-TNF-alpha antibody is 0.75 to 7.5 mg/kg of body weight.

The present invention can also utilize a specific binding agent and any of one or more Non-Steroidal Anti-Inflammatory Drugs (NSAIDs). NSAIDs owe their anti-inflammatory action, at least in part, to the inhibition of prostaglandin synthesis. Goodman and Gilman, The Pharmacological Basis of Therapeutics, MacMillan 7th Edition (1985). NSAIDs can be characterized into nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones. Examples of NSAIDs include, but are not limited to: Anaprox™, Anaprox DS™ (naproxen sodium); Ansaid™ (flurbiprofen); Arthrotec™ (diclofenac sodium+misoprostil); Cataflam™/Voltaren™ (diclofenac potassium); Clinoril™ (sulindac); Daypro™ (oxaprozin); Disalcid™ (salsalate); Dolobid™ (diflunisal); EC Naprosyn™ (naproxen sodium); Feldene™ (piroxicam); Indocin™, Indocin SR™ (indomethacin); Lodine™, Lodine XL™ (etodolac); Motrin™ (ibuprofen); Naprelan™ (naproxen); Naprosyn™ (naproxen); Orudis™, (ketoprofen); Oruvail™ (ketoprofen); Relafen™ (nabumetone); Tolectin™, (tolmetin sodium); Trilisate™ (choline magnesium trisalicylate); Cox-1 inhibitors; Cox-2 Inhibitors such as Vioxx™ (rofecoxib); Arcoxia™ (etoricoxib), Celebrex™ (celecoxib); MobiC™ (meloxicam); Bextra™ (valdecoxib), Dynastat™ paracoxib sodium; Prexige™ (lumiracoxib), and nambumetone. Additional suitable NSAIDs, include, but are not limited to, the following: .epsilon.-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixim, lefetamine HCl, leflunomide, lofemizole, lotifazole, lysin clonixinate, meseclazone, nabumetone, nictindole, nimesulide, orgotein, orpanoxin, oxaceprolm, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, A177B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO.sub.3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also encompassed by this group.

Suitable SAARDs or DMARDS include, but are not limited to: allocupreide sodium, auranofin, aurothioglucose, aurothioglycamide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

Inhibitors of kinases in signaling cascades are also suitable agents for combination with the specific binding agents of the invention. These include, but are not limited to, agents which are capable of inhibiting P-38 (a.k.a., "RK" or "SAPK-2", Lee et al., Nature, 372:739 (1994). P-38 is described as a serine/threonine kinase (see Han et al., Biochimica Biophysica Acta, 1265:224-227 (1995). Inhibitors of P-38 have been shown to intervene between the extracellular stimulus and the secretion of IL-1 and TNF-alpha from the cell involves blocking signal transduction through inhibition of a kinase which lies on the signal pathway.

Additionally suitable are MK2 inhibitors, and tpl-2 inhibitors. Additionally, T-cell inhibitors are also suitable, including, for example, ctla-4, CsA, Fk-506, OX40, OX40R-Fc, OX40 antibody, OX40 ligand, OX40 ligand antibody, lck, and ZAP70. Also suitable are retinoids, including oral retinoids, as well as antagonists of TGF-beta.

Further suitable agents for combination with the specific binding agents of the invention include, for example, any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate and sulfasalazine. Structurally related salicylic acid derivatives having similar analgesic and anti-inflammatory properties are also intended to be encompassed by this group. Additionally suitable agents include, for example propionic acid derivatives, prodrug esters or pharmaceutically acceptable salts thereof. The propionic acid derivatives, prodrug esters and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group. Also suitable for use are acetic acid derivatives, prodrug esters or pharmaceutically acceptable salts thereof. The acetic acid derivatives, prodrug esters and pharmaceutically acceptable salts thereof comprise: acemetacin, alclofenac, amfenac, bufexamac, cinmetacin, clopirac, delmetacin, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, zidometacin and zomepirac. Structurally related acetic acid derivatives having similar analgesic and anti-inflammatory properties are also intended to be encompassed by this group. Further suitable for use as described herein are fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefanamic acid, niflumic acid, talniflumate, terofenamate, tolfenamic acid and ufenamate. Structurally related fenamic acid derivatives having similar analgesic and anti-inflammatory properties are also intended to be encompassed by this group.

Also suitable are carboxylic acid derivatives, prodrug esters and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group. Additionally suitable are butyric acid derivatives, prodrug esters or pharmaceutically acceptable salts thereof. The butyric acid derivatives, prodrug esters and pharmaceutically acceptable salts thereof comprise: bumadizon, butibufen, fenbufen and xenbucin. Structurally related butyric acid derivatives having similar analgesic and anti-inflammatory properties are also intended to be encompassed by this group. Oxicams, prodrug esters or pharmaceutically acceptable salts thereof are also suitable. Oxicams, prodrug esters and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group. Pyrazoles, prodrug esters or pharmaceutically acceptable salts thereof are also suitable. The pyrazoles, prodrug esters and pharmaceutically acceptable salts thereof which may be used comprise: difenamizole and epirizole. Structurally related pyrazoles having similar analgesic and anti-inflammatory properties are also intended to be encompassed by this group. Furthermore, pyrazolones, prodrug esters or pharmaceutically acceptable salts thereof are suitable. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

Also suitable are prodrug esters or pharmaceutically acceptable salts thereof for the treatment of TNF-mediated diseases. Corticosteroids, prodrug esters and pharmaceutically acceptable salts thereof include hydrocortisone and compounds which are derived from hydrocortisone, such as 21-acetoxy-pregnenolone, alclomerasone, algestone, amcinonide, beclomethasone, beta-methasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydro-cortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

Antimicrobials (and prodrug esters or pharmaceutically acceptable salts thereof) are also suitable for combination use as described herein. Suitable antimicrobials include, for example, ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillan, erythromycin, flucloxacillan, gentamicin, gramicidin, methicillan, neomycin, oxacillan, penicillin and vancomycin. Structurally related antimicrobials having similar analgesic and anti-inflammatory properties are also intended to be encompassed by this group.

Additional suitable compounds include, but are not limited to: BN 50730; tenidap; E 5531; tiapafant PCA 4248; nimesulide; panavir; rolipram; RP 73401; peptide T; MDL 201, 449A; (1R,3S)-Cis-1-[9-(2,6-diamin-opurinyl)]-3-hydroxy-4-cyclopentene hydrochloride; (1R,3R)-trans-1-[9-(2,6-diamino)purine]-3-acetoxycyclopentane; (1R,3R)-trans-1-[9-adenyl]-3-azido-cyclopentane hydrochloride and (1R,3R)-trans-1-[6-hydroxy-purin-9-yl)-3-azidocyclopentane.

It has been found that IL-4 can induce an inflammatory effect in some instances, such as in asthma, in which overexpression of IL-4 in the lungs causes epithelial cell hypertrophy and an accumulation of lymphocytes, eosinophils, and neutrophils. This response is representative of the main features of the proinflammatory response induced by other Th2 cytokines. As noted above, therefore, inhibitors of IL-4 are also useful in accordance with the invention. Additionally, it will be appreciated that certain immunosuppressant drugs can also be used in the treatment of arthritis, including, but not limited to, iNOS inhibitors, and 5-lipoxygenase inhibitors.

Ginger has been shown to have certain anti-inflammatory properties, and is therefore suitable for use as an anti-inflammatory agent in accordance with the invention, as is chondroitin.

Pharmaceutical compositions of the invention also can be administered in combination therapy, i.e., in combination with other agents and therapies, in the treatment of diseases associated with CD148 activation. The antibodies and antigen-binding regions of the present invention can also be utilized in combination with other agents and therapies to treat cancers or tumors. Such agents include, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth. Other therapies also include, for example radiation treatment, chemotherapy, and targeted therapies with anti-tumor agents, and the like. In a particular embodiment, the human anti-CD148 antibodies, or antigen binding fragments thereof, can be administered in combination with one or more therapeutic agent, e.g., an anti-angiogenic agent, an anti-neoplastic agent, a chemotherapeutic agent, an immunosuppressive agent, an anti-inflammatory agent, or an anti-psoriasis agent. The human anti-CD148 antibodies, or antigen binding fragments thereof, can also be administered in combination with other known therapies, such as physical therapies, e.g., radiation therapy, hyperthermia, transplantation (e.g., bone marrow transplantation), surgery, sunlight, or phototherapy. Additional combination therapies not specifically listed herein are also within the scope of the present invention.

Exemplary anti-neoplastic agents include, for example, doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/m$^2$ dose once every four weeks and adriamycin is intravenously administered as a 60-75 mg/m$^2$ dose once every 21 days. Other exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Other anti-neoplastic agents that can be employed in combination chemotherapy treatment include, for example, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine-, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (M1H) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie-2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Other exemplary anti-angiogenic agents include antagonists of Ang-1 and CD148 (and their receptors), VEGF (Avastin, VEGF-TRAP, etc.), VEGF receptors, and IL-8, B-FGF, and small molecule inhibitors of KDR and other mediators of angiogenesis.

Additional anti-angiogenic/anti-tumor agents include: SD-7784 (Pfizer, USA); cilengitide (Merck KGaA, Germany, EPO 770622); pegaptanib octasodium (Gilead Sciences, USA); Alphastatin (BioActa, UK); M-PGA (Celgene, USA, U.S. Pat. No. 5,712,291); ilomastat, (Arriva, USA, U.S. Pat. No. 5,892,112); emaxanib (Pfizer, USA, U.S. Pat. No. 5,792,783); vatalanib (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands) DAC:antiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 970070); ARGENT technology (Ariad, USA); YIGSR-Stealth (Johnson & Johnson, USA); fibrinogen-E fragment (BioActa, UK); angiogenesis inhibitor (Trigen, UK); TBC-1635 (Encysive Pharmaceuticals, USA); SC-236 (Pfizer, USA); ABT-567 (Abbott, USA); Metastatin (EntreMed, USA); angiogenesis inhibitor, (Tripep, Sweden); maspin (Sosei, Japan); 2-methoxyestradiol (Oncology Sciences Corporation, USA); ER-68203-00 (IVAX, USA); Benefin (Lane Labs, USA); Tz-93 (Tsumura, Japan); TAN-1120 (Takeda, Japan); FR-11142 (Fujisawa, Japan, JP 02233610); platelet factor 4 (RepliGen, USA, EP 407122); vascular endothelial growth factor antagonist (Borean, Denmark); cancer therapy (University of South Carolina, USA); bevacizumab (PINN) (Genentech, USA); angiogenesis inhibitors (SUGEN, USA); XL 784 (Exelixis, USA); XL 647 (Exelixis, USA); MAb, alpha5beta3 integrin, second generation (Applied Molecular Evolution, USA and MedImmune, USA); gene therapy, retinopathy (Oxford BioMedica, UK); enzastaurin hydrochloride (USAN) (Lilly, USA); CEP 7055 (Cephalon, USA and Sanofi-Synthelabo, France); BC 1 (Genoa Institute of Cancer Research, Italy); angiogenesis inhibitor (Alchemia, Australia); VEGF antagonist (Regeneron, USA); rBPI 21 and BPI-derived antiangiogenic (XOMA, USA); PI 88 (Progen, Australia); cilengitide (pINN) (Merck KGaA, German; Munich Technical University, Germany, Scripps Clinic and Research Foundation, USA); cetuximab (INN) (Aventis, France); AVE 8062 (Ajinomoto, Japan); AS 1404 (Cancer Research Laboratory, New Zealand); SG 292 (Telios, USA); Endostatin (Boston Childrens Hospital, USA); ATN 161 (Attenuon, USA); ANGIOSTATIN (Boston Childrens Hospital, USA); 2-methoxyestradiol (Boston Childrens Hospital, USA); ZD 6474 (AstraZeneca, UK); ZD 6126 (Angiogene Pharmaceuticals, UK); PPI 2458 (Praecis, USA); AZD 9935 (AstraZeneca, UK); AZD 2171 (AstraZeneca, UK); vatalanib (pINN) (Novartis, Switzerland and Schering AG, Germany); tissue factor pathway inhibitors (EntreMed, USA); pegaptanib (Pinn) (Gilead Sciences, USA); xanthorrhizol (Yonsei University, South Korea); vaccine, gene-based, VEGF-2 (Scripps Clinic and Research Foundation, USA); SPV5.2 (Supratek, Canada); SDX 103 (University of California at San Diego, USA); PX 478 (ProlX, USA); METASTATIN (EntreMed, USA); troponin I (Harvard University, USA); SU 6668 (SUGEN, USA); OXI 4503 (OXiGENE, USA); o-guanidines (Dimensional Pharmaceuticals, USA); motuporamine C (British Columbia University, Canada); CDP 791 (Celltech Group, UK); atiprimod (pINN) (GlaxoSmithKline, UK); E 7820 (Eisai, Japan); CYC 381 (Harvard University, USA); AE 941 (Aeterna, Canada); vaccine, angiogenesis (EntreMed, USA); urokinase plasminogen activator inhibitor (Dendreon, USA); oglufamide (pINN) (Melmotte, USA); HIF-lalfa inhibitors (Xenova, UK); CEP 5214 (Cephalon, USA); BAY RES 2622 (Bayer, Germany); Angiocidin (InKine, USA); A6 (Angstrom, USA); KR 31372 (Korea Research Institute of Chemical Technology, South Korea); GW 2286 (GlaxoSmithKline, UK); EHT 0101 (ExonHit, France); CP 868596 (Pfizer, USA); CP 564959 (OSI, USA); CP 547632 (Pfizer, USA); 786034 (GlaxoSmithKline, UK); KRN 633 (Kirin Brewery, Japan); drug delivery system, intraocular, 2-methoxyestradiol (EntreMed, USA); anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors (National Institute on Aging, USA); SU 11248 (Pfizer, USA and SUGEN USA); ABT 518 (Abbott, USA); YH16 (Yantai Rongchang, China); S-3APG (Boston Childrens Hospital, USA and EntreMed, USA); MAb KDR, (ImClone Systems, USA); MAb alpha5 beta1 (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); MAb vascular endothelium growth factor (Xenova, UK); irsogladine (INN) (Nippon Shinyaku, Japan); RG 13577 (Aventis, France); WX 360 (Wilex, Germany); squalamine (PINN) (Genaera, USA); RPI 4610 (Sima, USA); cancer therapy (Marinova, Australia); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VEGF receptor modulators (Pharmacopeia, USA); VE-cadherin-2 antagonists (ImClone Systems, USA); Vasostatin (National Institutes of Health, USA);vaccine, Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); thrombospondin 1 inhibitor (Allegheny Health, Education and Research Foundation, USA).

The pharmaceutical compositions of the present invention can also include one or more inhibitors of growth factor agents, such as antagonists of hepatocyte growth factor (HGF, also known as Scatter Factor, and its receptor "c-met").

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CD148, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti- CD148 antibodies linked to anti-FcγRI or anti-CD3 may be used in conjunction with IgG- or IgA-receptor specific binding agents.

Bispecific and multispecific molecules of the invention can also be used to modulate FcαR or FcγR levels on effector cells, such as by capping and elimination of receptors on the cell surface. Mixtures of anti-Fc receptors can also be used for this purpose.

The compositions (e.g., human antibodies, multispecific and bispecific molecules) of the invention which have complement binding sites, such as portions from IgG1, IgG2, IgG3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Also within the scope of the invention are kits comprising the compositions (e.g., human antibodies, multispecific and bispecific molecules) of the invention and instructions for use. The kit can further contain a least one additional reagent, such as complement, or one or more additional human antibodies of the invention (e.g., a human antibody having a complementary activity which binds to an epitope in CD148 antigen distinct from the first human antibody).

In other embodiments, the subject can be additionally treated with an agent that modulates, e.g., enhances or inhibits, the expression or activity of Fcα or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

In another embodiment, the subject can be additionally treated with a lymphokine preparation. Cancer cells which do not highly express CD148 can be induced to do so using lymphokine preparations. Lymphokine preparations can cause a more homogeneous expression of CD148s among cells of a tumor which can lead to a more effective therapy. Lymphokine preparations suitable for administration include interferon-gamma, tumor necrosis factor, and combinations thereof. These can be administered intravenously. Suitable dosages of lymphokine are 10,000 to 1,000,000 units/patient.

The compositions (e.g., human antibodies, multispecific and bispecific molecules) of the invention can also be used to target cells expressing FcγR or CD148, for example for labeling such cells. For such use, the binding agent can be linked to a molecule that can be detected. Thus, the invention provides methods for localizing ex vivo or in vitro cells expressing Fc receptors, such as FcγR, or CD148. The detectable label can be, e.g., a radioisotope, a fluorescent compound, an enzyme, or an enzyme co-factor.

In one embodiment, the invention provides methods for detecting the presence of CD148 antigen in a sample, or measuring the amount of CD148 antigen, comprising contacting the sample, and a control sample, with a human monoclonal antibody, or an antigen-binding region thereof, which specifically binds to CD148, under conditions that allow for formation of a complex between the antibody or portion thereof and CD148. The formation of a complex is then detected, wherein a difference complex formation between the sample compared to the control sample is indicative the presence of CD148 antigen in the sample.

In still another embodiment, the invention provides a method for detecting the presence or quantifying the amount of Fc-expressing cells in vivo or in vitro. The method comprises (i) administering to a subject a composition (e.g., a multi- or bispecific molecule) of the invention or a fragment thereof, conjugated to a detectable marker; (ii) exposing the subject to a means for detecting said detectable marker to identify areas containing Fc-expressing cells.

Uses and Methods of the Invention

The present invention provides antibodies or antigen-binding regions thereof that bind to CD148 epitopes that are useful for the treatment of human diseases and pathological conditions. Agents that activate CD148 activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of CD148 activity in a cell. These diseases include cancers, and other hyperproliferative conditions, such as hyperplasia, psoriasis, contact dermatitis, immunological disorders, and infertility.

The compositions (e.g., human antibodies, multispecific and bispecific molecules) of the invention can be initially tested for binding activity associated with therapeutic or diagnostic use in vitro. For example, compositions of the invention can be tested using the ELISA and flow cytometric assays described herein. Moreover, the activity of these molecules in triggering at least one effector-mediated effector cell activity, including cytolysis of cells expressing CD148 can be assayed. Protocols for assaying for effector cell-mediated phagocytosis are described herein.

The compositions (e.g., human antibodies, multispecific and bispecific molecules) of the invention have additional utility in therapy and diagnosis of CD148-related diseases. For example, the human monoclonal antibodies, the multispecific or bispecific molecules can be used to promote CD148 inducted dephosphorylation in a cell expressing CD148, to inhibit the growth of a cell expressing CD148, or to inhibit angiogenesis of a cell expressing CD148. The anti-CD148 antibodies of the present invention may be useful in treating any angiogenesis-dependant disease, including, but not limited to, ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example, so-called solid tumors and liquid (or hematopoietic) tumors (such as leukemias and lymphomas). Other diseases associated with undesired angiogenesis will be apparent to those skilled in the art.

In a particular embodiment, the human antibodies and derivatives thereof are used in vivo to treat, prevent or diagnose a variety of CD148-related neoplastic diseases. Examples of CD148-related diseases include a variety of cancers, such as bladder, breast, uterine/cervical, colon, pancreatic, colorectal, kidney, stomach, ovarian, prostate, renal cell, squamous cell, lung (non-small cell), esophageal, and head and neck cancer.

The present invention also provides methods of treating cancer in an animal, including humans, comprising administering to the animal an effective amount of an antibody or antigen-binding region thereof that activates CD148 activity. The invention is further directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention are also readily adaptable for use in assay systems, e.g., assaying cancer cell growth and properties thereof, as well as identifying compounds that affect cancer cell growth.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells that infiltrate (invade) the surrounding tissues and give rise to metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The type of cancer or tumor cells amenable to treatment according to the invention include, for example, ACTH-producing tumor, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and non-small cell), malignant peritoneal effusion, malignant pleural effusion, melanoma, mesothelioma, multiple myeloma, neuroblastoma, glioma, non-Hodgkin's lymphoma, osteosarcoma, ovarian cancer, ovarian (germ cell) cancer, pancreatic cancer, penile cancer, prostate cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva, and Wilms' tumor.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any solid tumor derived from any organ system. Cancers whose invasiveness or metastasis is associated with CD148 activity are especially susceptible to being inhibited or even induced to regress by means of the invention.

The invention can also be practiced by including with a compound of the invention such as a peptibody in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

The present invention thus provides compositions and methods useful for the treatment of a wide variety of cancers, including solid tumors and leukemias. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); histiocytic disorders; leukemia; histiocytosis malignant; Hodgkin's disease; immunoproliferative small lung cell carcinoma; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; tophoblastic tumor. Further, the following types of cancers may also be treated: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Another aspect of the present invention is using the materials and methods of the present invention to prevent and/or treat any hyperproliferative condition of the skin including psoriasis and contact dermatitis or other hyperproliferative diseases. Preferably, specific binding agents specific for CD148 will be used in combination with other pharmaceutical agents to treat humans that express these clinical symptoms. The specific binding agents can be delivered using any of the various carriers through routes of administration described herein and others that are well known to those of skill in the art.

Other aspects of the present invention include treating various retinopathies (including diabetic retinopathy and age-related macular degeneration) in which angiogenesis is involved, as well as disorders/diseases of the female reproductive tract such as endometriosis, uterine fibroids, and other such conditions associated with dysfunctional vascular proliferation (including endometrial microvascular growth) during the female reproductive cycle.

Still another aspect of the present invention relates to treating abnormal vascular growth including cerebral arterioyenous malformations (AVMs) gastrointestinal mucosal injury and repair, ulceration of the gastroduodenal mucosa in patients with a history of peptic ulcer disease, including ischemia resulting from stroke, a wide spectrum of pulmonary vascular disorders in liver disease and portal hypertension in patients with nonhepatic portal hypertension.

Another aspect of present invention is the prevention of cancers utilizing the compositions and methods provided by the present invention. Such reagents will include specific binding agents such as antibodies, or antigen-binding regions thereof, against CD148.

Identification of CD148 Epitope Binding Molecules

The CD148 epitopes and antibodies of the present invention may be used to identify agents that activate CD148 activity, which may be useful in treating certain physiological disorders, including, but not-limited to inhibiting angiogenesis. In one aspect of the present invention there is provided a method for identifying a compound that specifically binds to a human CD148 epitope defined by one or more of the polypeptide sequences selected from the group consisting of amino acids 447-725, 533-725, 715-973, 324-335, 200-536, 533-725 and 200-725 of SEQ ID NO:33, comprising: contacting a test compound with a human CD148 epitope defined by one or more of the polypeptide sequences selected from the group consisting of amino acids 447-725, 533-725, 715-973, 324-335, 200-536, 533-725 and 200-725 of SEQ ID NO:33 for a time sufficient to form a complex and detecting for the formation of a complex by detecting the CD148 epitope or the compound in the complex, so that if a complex is detected, a compound that binds to the CD148 epitope is identified. For example, cells transfected with DNAs coding for proteins of interest can be treated with various drugs, and co-immunoprecipitations can be performed. Because CD148 is involved in transducing physiologicals signals asssociated with inhibition of such physiological disorders as angiogenesis, the identification of agents which are capable of activating CD148 activity will provide agents which can be used to treat physiological disorder or to use lead compounds for development of therapeutic agents. An agent may activate CD148 by binding to the CD148 epitopes defined herein in such a manner that the agent initiates CD148 dephosphorylation. Agents which may be used to active CD148 include peptides, antibodies, nucleic acids, antisense compounds or ribozymes. The nucleic acid may encode the antibody or the antisense compound. The peptide may be at least 4 amino acids of the sequence of the binding protein. Alternatively, the peptide may be from 4 to 30 amino acids (or from 8 to 20 amino acids) that is at least 75% identical to a contiguous span of amino acids of the binding protein. Agents can be tested using transfected host cells, cell lines, cell models or animals, such as described herein, by techniques well known to those of ordinary skill in the art, such as disclosed in U.S. Pat. Nos. 5,622,852 and 5,773,218, and PCT published application Nos. WO 97/27296 and WO 99/65939, each of which are incorporated herein by reference. The modulating effect of the agent can be tested in vivo or in vitro. Agents can be provided for testing in a phage display library or a combinatorial library. Exemplary of a method to screen agents is to measure the effect that the agent has on the formation of the protein complex.

The CD148 epitopes of the present invention may also be used to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. One aspect of the present invention provides a method for identifying a compound that specifically binds to a human CD148 epitope defined by one or more of the polypeptide sequences selected from the group consisting of amino acids 447-725, 533-725, 715-973, 324-335, 200-536, 533-725 and 200-725 of SEQ ID NO:33 comprising: providing atomic coordinates defining a three-dimensional structure of a CD148 epitope defined by one or more of the polypeptide sequences selected from the group consisting of amino acids 447-725, 533-725, 715-973, 324-335, 200-536, 533-725 and 200-725 of SEQ ID NO:33, and designing or selecting compounds capable of binding the CD148 epitope based on said atomic coordinates. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetic to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

Binding Assays

Immunological binding assays typically utilize a capture agent to bind specifically to and often immobilize the analyte target antigen. The capture agent is a moiety that specifically binds to the analyte. In one embodiment of the present invention, the capture agent is an antibody or antigen-binding region thereof that specifically binds the CD148 epitopes of the invention. These immunological binding assays are well known in the art [Asai, ed., Methods in Cell Biology, Vol. 37, Antibodies in Cell Biology, Academic Press, Inc., New York (1993)].

Immunological binding assays frequently utilize a labeling agent that will signal the existence of the bound complex formed by the capture agent and antigen. The labeling agent can be one of the molecules comprising the bound complex; i.e. it can be a labeled specific binding agent or a labeled anti-specific binding agent antibody. Alternatively, the labeling agent can be a third molecule, commonly another antibody, which binds to the bound complex. The labeling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent. These binding proteins are normal constituents of the cell walls of streptococcal bacteria and exhibit a strong non-immunogenic reactivity with immunoglobulin constant regions from a variety of species. Akerstrom, J. Immunol., 135:2589-2542 (1985); Chaubert, Mod. Pathol., 10:585-591 (1997).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

A. Non-Competitive Binding Assays:

Immunological binding assays can be of the non-competitive type. These assays have an amount of captured analyte that is directly measured. For example, in one preferred "sandwich" assay, the capture agent (antibody) can be bound directly to a solid substrate where it is immobilized. These immobilized capture agents then capture (bind to) antigen present in the test sample. The protein thus immobilized is then bound to a labeling agent, such as a second antibody having a label. In another preferred "sandwich" assay, the second antibody lacks a label, but can be bound by a labeled antibody specific for antibodies of the species from which the second antibody is derived. The second antibody also can be modified with a detectable moiety, such as biotin, to which a third labeled molecule can specifically bind, such as streptavidin. See Harlow and Lane, Antibodies, A Laboratory Manual, Ch 14, Cold Spring Harbor Laboratory, N.Y. (1988), incorporated herein by reference.

B. Competitive Binding Assays:

Immunological binding assays can be of the competitive type. The amount of analyte present in the sample is measure indirectly by measuring the amount of an added analyte displaced, or competed away, from a capture agent (antibody) by the analyte present in the sample. In one preferred competitive binding assay, a known amount of analyte, usually labeled, is added to the sample and the sample is then contacted with the capture agent. The amount of labeled analyze bound to the antibody is inversely proportional to the concentration of analyte present in the sample (See, Harlow and Lane, Antibodies, A Laboratory Manual, Ch 14, pp. 579-583, supra).

In another preferred competitive binding assay, the capture agent is immobilized on a solid substrate. The amount of protein bound to the capture agent may be determined either by measuring the amount of protein present in a protein/antibody complex, or alternatively by measuring the amount of remaining uncomplexed protein. The amount of protein may be detected by providing a labeled protein. Harlow and Lane (supra).

Yet another preferred competitive binding assay, hapten inhibition is utilized. Here, a known analyte is immobilized on a solid substrate. A known amount of antibody is added to the sample, and the sample is contacted with the immobilized analyte. The amount of antibody bound to the immobilized analyte is inversely proportional to the amount of analyte present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

C. Utilization of Competitive Binding Assays:

The competitive binding assays can be used for cross-reactivity determinations to permit a skilled artisan to determine if a protein or enzyme complex which is recognized by a peptibody of the invention is the desired protein and not a cross-reacting molecule or to determine whether the peptibody is specific for the antigen and does not bind unrelated antigens. In assays of this type, antigen can be immobilized to a solid support and an unknown protein mixture is added to the assay, which will compete with the binding of the peptibodies to the immobilized protein. The competing molecule also binds one or more antigens unrelated to the antigen. The ability of the proteins to compete with the binding of the peptibodies to the immobilized antigen is compared to the binding by the same protein that was immobilized to the solid support to determine the cross-reactivity of the protein mix.

D. Other Binding Assays

The present invention also provides Western blot methods to detect or quantify the presence of a CD148 epitope or fragment thereof in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with antibodies or antigen-binding regions thereof that specifically bind a CD148 epitope and the resulting complex is detected. These peptibodies may be directly labeled or alternatively may be subsequently detected using labeled antibodies that specifically bind to the peptibody.

E. Diagnostic Assays

The derivative binding agents, such as peptides and peptibodies or fragments thereof, of the present invention are useful for the diagnosis of conditions or diseases characterized by expression of CD148 or subunits, or in assays to monitor patients being treated with activators of CD148, its fragments, agonists or inhibitors of CD148 activity. Diagnostic assays for CD148 include methods utilizing an antibody and a label to detect CD148 in human body fluids or extracts of cells or tissues. The antibodies of the present invention can be used with or without modification. In a preferred diagnostic assay, the antibodies will be labeled by attaching, e.g., a label or a reporter molecule. A wide variety of labels and reporter molecules are known, some of which have been already described herein. In particular, the present invention is useful for diagnosis of human disease.

A variety of protocols for measuring CD148 proteins using antibodies specific for the respective protein are known in the art. Examples include enzyme-linked immunosorbent assay (ELISA), radioimmunoassay (RIA) and fluorescence activated cell sorting (FACS). A two-site, monoclonal-based immunoassay utilizing monoclonal antibodies reactive to two non-interfering epitopes on CD148 is preferred, but a competitive binding assay can be employed. These assays are described, for example, in Maddox et al., J. Exp. Med., 158: 1211 (1983).

In order to provide a basis for diagnosis, normal or standard values for human CD148 expression are usually established. This determination can be accomplished by combining body fluids or cell extracts from normal subjects, preferably human, with an antibody to CD148, under conditions suitable for complex formation that are well known in the art. The amount of standard complex formation can be quantified by comparing the binding of the antibodies to known quantities of CD148 protein, with both control and disease samples. Then, standard values obtained from normal samples can be compared with values obtained from samples from subjects potentially affected by disease. Deviation between standard and subject values suggests a role for CD148 in the disease state.

For diagnostic applications, in certain embodiments antibodies, or antigen-binding regions thereof, of the present invention typically will be labeled with a detectable moiety. The detectable moiety can be any one that is capable of producing, either directly or indirectly, a detectable signal. For example, the detectable moiety may be a radioisotope, such as $^3$H, $^4$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, beta-galactosidase, or horseradish peroxidase. Bayer et al., Meth. Enz., 184: 138-163, (1990).

The present invention is further illustrated by the following examples which should not be construed as further limiting. The contents of all figures and all references, patents and published patent applications cited throughout this application are expressly incorporated herein by reference.

EXAMPLE 1

Generation of Antibodies Against CD148 Epitopes

Parental versions of the heavy and light chains regions of the antibodies of the present invention were identified using the following screening procedure. Recombinant scFv (single chain variable fragment) phage display libraries from Cambridge Antibody Technologies (CAT) were interrogated in vitro against huCD148 protein targets. Over 10,000 clones were screened, recovered by phage display ($2^{nd}$ and $3^{rd}$ round outputs) and greater than 250 unique scFv antibodies were identified that specifically bind huCD148. Of these reagents, 83 were consolidated for further study, based upon their predicted therapeutic potential. For example, several antibodies were isolated that compete for binding to the same epitope as that of N24 as measured by competitive ELISA or TRF (time-resolved fluorescence) report. Other antibodies were consolidated based upon their relatively high signal-to-noise ratio as indicated by ELISA or TRF (e.g., target binding compared to streptavidin binding) or because they cross-reacted to the murine CD148 ortholog. All anti-CD148 antibodies were tested for their ability to cross-react with muCD148 (for in vivo mouse studies) and to bind cell-expressed huCD148. Eight scFv human N24 analog antibodies exhibiting the relatively highest degree of competition with N24 as either IgG4s, maxibodies (bivalent scFv-Fcs) or both, as well as 7 other clones, were expressed and binding activity and specificity was confirmed. The original mouse N24 antibody was cloned, and the $V_H$ and $V_L$ genes were subcloned into various antibody "platforms" to serve as positive controls in comparative binding (i.e., ELISA or FACS) and functional in vitro and in vivo assays. Primary functional screening of the initial "top 14" leading candidate antibodies was completed. Eight of these clones agonize huCD148 in an in vitro planar migration assay. Moreover, 4 of these lead clones that cross-react to muCD148 inhibit FGF-2 induced angiogenesis in an in vivo mouse corneal pocket assay. The eight antibodies described in FIGS. 1-8 were capable of inhibiting angiogenesis in both a human endothelial cell migration assay and in a corneal pocket assay, with at least 20% capability as compared with controls in vitro at a concentration of 20 μg/ml.

The antibodies generated in accordance with the above procedure are described in the FIGS. 1-8. FIGS. 1A and 1B show a nucleotide and encoded amino acid sequence overlap for variable heavy (VH) and variable light (VL) chains for an antibody of the present invention, Antibody No. 1 (Ab-1). Shaded regions on the figure highlight CDR1, 2, and 3 (from amino to carboxy terminus, respectively). Query and Frame1 designations indicate the nucleotide and amino acid sequences, respectively.

FIGS. 2A and 2B show a nucleotide and encoded amino acid sequence overlap for variable heavy (VH) and variable light (VL) chains for Antibody No. 2 (Ab-2). Shaded regions on the figure highlight CDR1, 2, and 3 (from amino to carboxy terminus, respectively).

FIGS. 3A and 3B show a nucleotide and encoded amino acid sequence overlap for variable heavy (VH) and variable light (VL) chains for Antibody No. 3 (Ab-3). Shaded regions on the figure highlight CDR1, 2, and 3 (from amino to carboxy terminus, respectively).

FIGS. 4A and 4B show a nucleotide and encoded amino acid sequence overlap for variable heavy (VH) and variable light (VL) chains for Antibody No. 4 (Ab-4). Shaded regions on the figure highlight CDR1, 2, and 3 (from amino to carboxy terminus, respectively).

FIGS. 5A and 5B show a nucleotide and encoded amino acid sequence overlap for variable heavy (VH) and variable light (VL) chains for Antibody No. 5 (Ab-5). Shaded regions on the figure highlight CDR1, 2, and 3 (from amino to carboxy terminus, respectively).

FIGS. 6A and 6B show a nucleotide and encoded amino acid sequence overlap for variable heavy (VH) and variable light (VL) chains for Antibody No. 6 (Ab-6). Shaded regions on the figure highlight CDR1, 2, and 3 (from amino to carboxy terminus, respectively).

FIGS. 7A and 7B show a nucleotide and encoded amino acid sequence overlap for variable heavy (VH) and variable light (VL) chains for Antibody No. 7 (Ab-7). Shaded regions on the figure highlight CDR1, 2, and 3 (from amino to carboxy terminus, respectively).

FIGS. 8A and 8B show a nucleotide and encoded amino acid sequence overlap for variable heavy (VH) and variable light (VL) chains for Antibody No. 8 (Ab-8). Shaded regions on the figure highlight CDR1, 2, and 3 (from amino to carboxy terminus, respectively).

EXAMPLE 2

Mapping of CD148 Binding Epitopes

Synthetic peptide 15-mers corresponding to the ectodomain of human CD148 primary protein sequence were synthesized and covalently N-linked to sectors on PVDF membranes. The composition of the various peptide sequences overlapped by 3 amino acids.

Peptide-containing membranes were preincubated with MeOH for 10 min, washed 3 times with PBST and incubated overnight with 4% milk in PBST. After 3 washes with PBST the membrane was incubated for 3 hours with 1 μM anti-CD148 antibody diluted in 4% milk. The membrane was washed again 3 times and then incubated for 1 hr with either anti-human Fc-HRP or anti-mouse Fc-HRP (Jackson). After 3 washes with PBST binding was detected using the Super Signal kit from Pierce.

Peptide-containing membranes were regenerated for new experiments by immediately washing them twice with water (after one use) and then incubating them overnight with DMF. After 2 washes with water the membrane was washed with regeneration buffer A (1% SDS, 0.1% b-mercaptoethanol, 8M Urea) for several hours, then it was washed 2 times with regeneration buffer B (50% EtOH, 10% Acetic Acid). The efficiency of the regeneration step was verified by staining the membrane using secondary antibody alone and developing. After completing the regeneration process, membranes were rinsed with MeOH, dried and stored in −20° C.

Binding of Ab-1, Ab-2, Ab-3, and Ab-5, a murine anti-CD148 antibody, and anti-CD148 antibody 143-41 (Biosource) to the peptide containing membranes was tested in accordance with the procedure described above, with the following results:

The murine antibody bound to peptides 114-117 in membrane #1 and 90-93 in membrane #2 (114 & 90: GPVDPSSGQQSRDTE (residues 315-329), 115 & 91: DPSSGQQSRDTEVLL (residues 318-332), 116 & 92: SGQQSRDTEVLLVGL (residues 321-335), 117 & 93: QSRDTEVLLVGLEPG (residues 324-338)), which have the common epitope QSRDTE (residues 324-329). The murine antibody also bound the octapeptide QSRDTEVLL (residues 324-332).

Ab-1 bound peptides 116 and 117 in membrane #1 and peptides 92 and 93 in membrane #2 (116 & 92: SGQQSRDTEVLLVGL (residues 321-335), 117 & 93: QSRDTEVLLVGLEPG (residues 324-338)), which have the common epitope QSRDTEVLLVGL (residues 324-335), but did not bind the octapeptide QSRDTEVL (residues 324-331). No other anti-CD148 antibodies that were tested showed evidence of binding to these peptide-containing membranes. Thus, Ab-1 antibody binds to a peptide having the sequence of amino acid residues 324-338 and 321-335, but does not bind to an octapeptide having the sequence of amino acid residues 324-331 of human CD148.

Based on the peptide mapping results the minimal required epitope of the murine anti-CD148 antibody was narrowed to the 6 amino acids QSRDTE (residues 324-329). The minimal required epitope of Ab-1 was also determined to be the 12 amino acids QSRDTEVLLVGL (residues 324-335). Because no other anti-CD148 antibodies tested showed binding to the peptide-containing membranes, it was determined that epitopes for those antibodies are structurally dependent.

EXAMPLE 3

Construction and Assay of FLAG, Poly-Histidine and Fc fusion Proteins

The following constructs were subcloned into the p412 mammalian expression vector flanked N-terminally by both an IgK leader sequence and Flag poly-Histidine tag fusions; huCD148-ECTO (residues 36-973); huCD148-NFnIII (residues 36-210); huCD148-FnII2_3 (residues 175-536); huCD148-FnIII4_5 (residues 533-725); huCD148-Cterm: (residues 715-973). These clones were transiently transfected into COS PKB (E5) cells and purified using an IMAC column.

The binding of different anti-CD148 antibodies was tested using 2 different ELISA methods. The first method is a direct ELISA on Ni-NTA plates. Ni-NTA plates (Invitrogen) were coated with 4 dilutions (1:10-1:10.000) of the 5 proteins in 3% BSA in PBS and were incubating overnight at 4° C. The plates were washed with PBST and incubated with 1 μg/ml of Ab-2-huIgG4, Ab-5-huIgG4, the murine anti-CD148 antibody, and 143-41 (Biosource) for 2 hrs at room temperature. After additional washes the plates were incubated with anti-hu-IgG4-HRP (Zymed) or anti-mouse-FC-HRP (Jackson) for 1 hr at room temperature. Then washed again and the signal was developed by adding 100 µl of 10 mg of ABTS (Amersham) with 45 ml 0.05M citric acid pH 4.0 and 77 µl of 30% $H_2O_2$.

The second method is an indirect ELISA. Maxisorp plates were coated with 5 µg/ml anti-huFc or anti-muFc (Jackson) overnight at 4° C. The plates were washed with PBST and blocked with 3% BSA in PBS for 1.5 hrs. After additional washes the plates were incubated with 5 ug/ml of Ab-2-huIgG4, Ab-5-huIgG4, murine anti-CD148 antibody, and 143-41 (Biosource) for 2 hrs at room temperature. The plates were washed again and were incubated with 2 dilutions (1:10, 1:100) of the 5 proteins for 2 hrs at room temperature, washed again and incubated with anti-FLAG M2-HRP (Sigma) for 1 hr at room temperature.

As expected, based upon peptide mapping, the murine anti-CD148 antibody bound the huCD148-FnIII2_3 protein (residues 175-536). The commercial 143-41 antibody (Biosource) binds to the huCD148-NFnIII protein (residues 36-210). In addition, Ab-5 binds to both the huCD148-FnIII4_5 protein (residues 533-725) and the huCD148-Cterm protein (residues 715-973).

Because the yield of the proteins using this method of purification was very low the FLAG poly-his tag was changed to that of an Fc tag. The constructs were again transfected into CHO PBK E5 cells, purified using protein A column and the binding of anti-CD148 antibodies was tested by another ELISA method. Maxisorp plates were coated with 5 µg/ml anti-huFc (Jackson) overnight at 4° C., washed and blocked with 3% milk in PBS for 1.5 hrs. The plates were washed again and incubated with 5 µg/ml of the different CD148-Fc constructs for 2 hrs at room temperature. After additional washes the plates were incubated with 1 µg/ml of Ab-2-huIgG4, Ab-5-huIgG4, Ab-1-huIgg4, murine anti-CD148 antibody, and 143-41 (Biosource) for 2 hrs at room temperature. Plates were washed again and incubated with anti-huIgG4-HRP (Zymed) or anti-mouse Fc-HRP (Jackson) for 1 hr at room temperature.

Five CD148 constructs with either Flag, Poly-His tags or Fc tag were expressed transiently in 293 E5 cells and were purified using IMAC column or protein A column respectively. Binding of anti-CD148 clones to the different constructs was tested by ELISA, as described in the methods. The human anti CD148 clone, Ab-5, bound both the FnIII4_5 (residues 533-725) piece and the C-term piece (residues 715-973) when the Flag, Poly-His tags constructs were used and to the FnIII4_5 (residues 533-725) when the Fc tag constructs were used. It also binds the full-length ECTO domain protein (residus 36-973) with both tags. The human anti-CD148 clone, Ab-2, showed binding to the full-length ECTO domain protein (residus 36-973) with both tags and a low level of binding to the FnIII4_5 (residues 533-725) with the Fc tag but no binding at all to any of the other 3 constructs. The human anti CD148 clone, Ab-1 was used only in the ELISA with the Fc constructs. It bound only the FnIII2_3 piece (residues 175-536. The commercial murine anti-CD148 143-41 (Biosource) bound the full-length ECTO domain protein (residus 36-973) and the NFnIII piece (residues 36-210) in all essays but didn't bind any of the other 3 constructs. The murine anti-CD148 antibody was used as a positive control in all essays since it was known to recognize the octapeptide in residues 324-332. The murine anti-CD148 antibody recognized the FnIII2_3 piece (residues 175-536) in all assays and the full-length ECTO domain protein (residus 36-973) with the Fc tag.

Based on the combined results of all 3 ELISAs it was concluded that the commercial murine anti-CD148 143-41 (Biosource) antibody recognizes a structurally depended epitope that lies within residues 36-210. Ab-5 recognized both the FnIII4_5 (residues 533-725) piece and the C-term piece (residues 715-973). These pieces have an overlap of 11 AA between them. Hence, these 11AA may be necessary for Ab-5 binding.

EXAMPLE 4

Construction and Assay of Avidin Fusion Proteins

The following constructs were subcloned into pCep4-Avidin-N vector: huCD148-NFnIII (residues 36-210); huCD148-FnIII2_3 (residues 36-536); huCD148-FnIII4_5 (2) (residues 36-715); huCD148-FnIII4_5 (residues 36-725); huCD148-ECTO (residues 36-973); huCD148FnIII2_3_4_5 (residues 200-725); huCD148FnIII3_4_5 (residues 447-725); huCD148-FnIII4_5 (only) (residues 533-725); huCD148-FnIII_5 (residues 616-725); huCD148-FnIII_5.5 (residues 672-725).

All avidin expression constructs were transfected into 293 T cells using Lipofectamine 2000 (Invitrogen) following the vendor protocol. The condition media was collected 2 days after the transfection and the level of Avidin-fused protein was determined using biotin beads (Spherotech Inc.). For each construct 511 of beads were used. The beads were pre-blocked by incubating with 3% BSA for 30 min at room temperature, washed once using 0.2% BSA in PBS and then added to 20011 of each of the condition media for an additional 1 hr incubation. After 2 washes, 1 µg/ml of anti-Avidin-FITC (Vector) was added for 30 minutes incubation, then the beads were washed again, resuspended in 500 µl wash buffer and read using FACS. Based on the expression level results the amount of condition media to be used in the binding essay was determined. The protocol for the binding assay is same as described above only instead of the anti-Avidn-FITC, 1 µg/ml of FITC labeled anti-CD148 Ab-2 and Ab-5 antibodies was added. A variation of this assay included co-incubation of the avidin fusion protein with both the FITC labeled antibody of interest as well as 50× excess unlabeled antibody to determine whether or not the unlabeled antibody can effectively compete/prevent for binding of the FITC-labeled antibody to be evaluated. This competition assay was and can be used to determine if any antibody can compete for binding to the same epitope space as another.

Both Ab-2 and Ab-5 recognized the full-length huCD148-ECTO (residues 36-973) and the huCD148-FnIII4_5 (residues 36-725) constructs. However, neither of these antibodies bind to the huCD148-NFnIII (residues 36-210), huCD148-FnIII2_3 (residues 36-536) and huCD148-FnIII4_5 (2) (residues 36-715) constructs. Ab-5 also bound the huCD148FnIII2_3_4_5 (residues 200-725); huCD148FnIII3_4_5 (residues 447-725) and huCD148-FnIII4_5 (only) (residues 533-725) constructs but not the huCD148-FnIII_5 (residues 616-725) and the huCD148-FnIII_5.5 (residues 672-725) constructs. Ab-2 bound huCD148FnIII2_3_4_5 (residues 200-725); huCD148FnIII3_4_5 (residues 447-725) constructs but did not bind huCD148-FnIII4_5 (only) (residues 533-725), huCD148-FnIII_5 (residues 616-725) and huCD148-FnIII_5.5 (residues 672-725) constructs.

In the competition assay Ab-2 was capable of fully inhibiting Ab-5 binding both to the huCD148-ECTO construct and to the FnIII4_5 construct. Ab-5 was able to fully compete the binding of Ab-2 to the huCD148-ECTO but only partially inhibits the binding of Ab-2 to huCD148-FnIII_4_5 constructs.

Because both Ab-2 and Ab-5 bind to the full-length huCD148-ECTO (residues 36-973) and the huCD148-FnIII4_5 (residues 36-725) constructs but not to the huCD148-FnIII4_5 (2) (residues 36-715) construct which only differ from the huCD148-FnIII4_5 (residues 36-725) construct by 11AA in the C-terminal end and because neither of these antibodies recognize any peptide in our peptide bound membranes, it was concluded that the 11AA in residues 715-725 are necessary for the binding of these antibodies but are not sufficient for the binding. Based on the binding results of these antibodies to constructs huCD148FnIII2_3_4_5 (residues 200-725), huCD148FnIII3_4_5 (residues 447-725), huCD148-FnIII4_5 (only) (residues 533-725), huCD148-FnIII_5 (residues 616-725) and huCD148-FnIII_5.5 (residues 672-725) it was determined that the minimum binding area for Ab-5 is residues 533-725 and for Ab-2 is residues 447-725.

EXAMPLE 5

Anti-Angiogenesis Activity of Anti-CD148 Antibodies in a Planar Migration Assay

A planar endothelial cell migration (wound closure) assay was used to quantitate the inhibition of angiogenesis in vitro by all antibodies disclosed in FIGS. 1-8, substantially as described in U.S. Pat. No. 6,248,327, which is incorporated herein by reference in its entirety. In this assay, endothelial cell migration is measured as the rate of closure of a circular wound in a cultured cell monolayer. The rate of wound closure is linear, and is dynamically regulated by agents that stimulate and inhibit angiogenesis in vivo.

Primary human renal microvascular endothelial cells, HRMEC, are isolated, cultured, and used at the third passage after thawing, as described in Martin et al., In Vitro Cell Dev Biol 33:261, 1997. Replicate circular lesions, "wounds," (600-800 micron diameter) are generated in confluent HRMEC monolayers using a silicon-tipped drill press. At the time of wounding the medium (DMEM+1% BSA) is supplemented with 20 ng/ml PMA (phorbol-12-myristate-13-acetate), alone or in the presence of 5 to 50 ug/ml of control or Ab-1 through Ab-8. The residual wound area is measured as a function of time (0-12 hours) using a microscope and image analysis software (Bioquant, Nashville, TN). The relative migration rate is calculated for each agent and combination of agents by linear regression of residual wound area plotted over time.

Each of Ab-1, Ab-2, Ab-3, Ab-4, Ab-5, Ab-6, Ab-7 and Ab-8 inhibited PMA-induced endothelial migration in a dose responsive manner, significantly reducing the rate of migration to unstimulated levels ranging from 15 to 50 ug/ml.

EXAMPLE 6

Anti-Angiogenesis Activity of Anti-CD148 Antibodies In a Corneal Pocket Assay

The ability of the antibodies of the present invention to inhibit angiogenesis in vivo was determined in a mouse corneal pocket assay, substantially as described in U.S. Pat. No. 6,248,327. In this assay, agents to be tested for angiogenic or anti-angiogenic activity are immobilized in a slow release form in a hydron pellet, which is implanted into micropockets created in the corneal epithelium of anesthetized mice. Vascularization is measured as the appearance, density, and extent of vessel ingrowth from the vascularized corneal limbus into the normally avascular cornea.

Polyvinyl alcohol sponge pellets containing FGF-2 (50 ng/pellet), bFGF and IgG (12 ug/pellet, control), or bFGF and Ab-1 to 8 (12 ug/pellet). The pellets were surgically implanted into corneal stromal micropockets created by micro-dissection 1 mm medial to the lateral corneal limbus of 6-8 week old male C57BL/6 mice. The pellets are surgically implanted into corneal stromal micropockets created by micro-dissection 1 mm medial to the lateral corneal limbus of 6-8 week old male C57BL mice. After five days, at the peak of neovascular response to FGF-2, the corneas are photographed using an MZ9.5 steriomicrosope (Leica) at an incipient angle of 35-50° from the polar axis in the meridian containing the pellet. Images are digitized and processed by subtractive color filters (Adobe Photoshop 4.0) to delineate established microvessels by hemoglobin content. Image analysis software (Bioquant, Nashville, Tenn.) is used to calculate the fraction of the corneal image that was vascularized, the vessel density within the vascularized area, and the vessel density within the total cornea.

Ab-2, Ab-4, Ab-5, and Ab-7 inhibited bFGF-induced corneal angiogenesis, significantly reducing the vascular density significantly to less than that induced by FGF alone.

What is claimed is:

1. An isolated monoclonal antibody or antigen-binding region thereof that specifically binds to a human CD148 epitope consisting of amino acids 447-725 or 533-725 of SEQ ID NO:33 wherein the amino acid residues 715-725 of said epitope are necessary for antibody binding, and wherein the monoclonal antibody or antigen binding region thereof inhibits angiogenesis.

2. The isolated monoclonal antibody or antigen-binding region thereof of claim 1, wherein the monoclonal antibody or antigen binding region thereof is a human antibody or antigen binding region thereof.

3. The isolated monoclonal antibody or antigen-binding region thereof of claim 1, wherein the monoclonal antibody or antigen binding region thereof is an antibody fragment selected from the group consisting of scFv, Fab, F(ab')$_2$, Fv, and single chain antibodies.

4. The isolated monoclonal antibody or antigen binding region thereof of claim 1, wherein the monoclonal antibody or antigen binding region thereof comprises a scFv fragment.

5. The isolated monoclonal antibody or antigen-binding region thereof of claim 1, wherein the monoclonal antibody or antigen-binding region thereof is an scFv-Fc fusion.

6. A hybridoma cell which produces a monoclonal antibody or antigen binding region thereof of claim 1.

7. A transfectoma cell which produces a monoclonal antibody or antigen binding region thereof of claim 1.

8. The isolated monoclonal antibody or antigen-binding region thereof of claim 1, produced by a hybridoma which includes a B cell obtained from a transgenic non-human animal having a genome comprising a human heavy chain transgene and a human light chain transgene fused to an immortalized cell.

9. The isolated monoclonal antibody or antigen-binding region thereof of claim 1, produced by a transfectoma comprising nucleic acids encoding a human heavy chain and a human light chain.

10. The monoclonal antibody or antigen binding region thereof produced by the hybridoma cell of claim 6.

11. The monoclonal antibody or antigen binding region thereof produced by the transfectoma cell of claim 7.

12. A pharmaceutical composition comprising the monoclonal antibody or antigen binding region thereof of claim 1 and a carrier pharmaceutically acceptable in humans.

13. The composition according to claim 12, wherein the monoclonal antibody or antigen binding region thereof is present in a therapeutically effective amount.

14. The composition according to claim 13, wherein the monoclonal antibody or antigen binding region thereof is present in a concentration of at least about 10 μg/ml.

15. The composition of claim 12, wherein the monoclonal antibody or antigen binding region thereof is a human monoclonal antibody.

16. The composition of claim 12, wherein the monoclonal antibody or antigen binding region thereof is an IgG monoclonal antibody or an antigen-binding region thereof.

17. The composition of claim 12, wherein the monoclonal antibody or antigen binding region thereof is a monoclonal antibody fragment selected from the group consisting of scFv, Fab, F(ab')$_2$, Fv, and single chain antibodies.

18. The composition of claim 12, wherein the monoclonal antibody or antigen binding region thereof comprises a scFv fragment.

19. The composition of claim 18, wherein the monoclonal antibody is an antibody or antigen binding region thereof comprises an scFv-Fc fusion.

* * * * *

SEQUENCE LISTING

```
<160> NUMBER OF SEQ ID NOS: 33

<210> SEQ ID NO 1
<211> LENGTH: 360
<212> TYPE: PRT
<213> ORGANISM: Homo sapiens

<400> SEQUENCE: 1

Gly Ala Gly Gly Thr Gly Cys Ala Gly Cys Thr Gly Thr Gly Gly
1               5                   10                  15

Ala Gly Thr Cys Thr Gly Gly Gly Gly Ala Gly Gly Cys Thr Thr
                20                  25                  30

Gly Gly Thr Ala Cys Ala Gly Cys Cys Thr Gly Gly Gly Gly Gly
                35                  40                  45
```

Thr Cys Cys Cys Thr Gly Ala Gly Ala Cys Thr Cys Thr Cys Thr
        50                  55                  60

Gly Thr Gly Cys Ala Gly Cys Cys Thr Cys Thr Gly Gly Ala Thr Thr
65                  70                  75                  80

Cys Ala Cys Cys Thr Thr Thr Ala Gly Cys Ala Gly Cys Thr Ala Thr
                    85                  90                  95

Gly Cys Cys Ala Thr Gly Ala Gly Cys Thr Gly Gly Gly Thr Cys Cys
                100                 105                 110

Gly Cys Cys Ala Gly Gly Cys Thr Cys Cys Ala Gly Gly Ala Ala
            115                 120                 125

Gly Gly Gly Gly Cys Thr Gly Gly Ala Gly Thr Gly Gly Gly Thr Cys
            130                 135                 140

Thr Cys Ala Gly Cys Thr Ala Thr Thr Ala Gly Thr Gly Gly Thr Ala
145                 150                 155                 160

Gly Thr Gly Gly Thr Gly Gly Thr Ala Gly Cys Ala Cys Ala Thr Ala
                165                 170                 175

Cys Thr Ala Cys Gly Cys Ala Gly Ala Cys Thr Cys Cys Gly Thr Gly
                180                 185                 190

Ala Ala Gly Gly Gly Cys Cys Gly Gly Thr Thr Cys Ala Cys Cys Ala
            195                 200                 205

Thr Cys Thr Cys Cys Ala Gly Ala Gly Ala Cys Ala Ala Thr Thr Cys
210                 215                 220

Cys Ala Ala Gly Ala Ala Cys Ala Cys Gly Cys Thr Gly Thr Ala Thr
225                 230                 235                 240

Cys Thr Gly Cys Ala Ala Ala Thr Gly Ala Ala Cys Ala Gly Cys Cys
                245                 250                 255

Thr Gly Ala Gly Ala Gly Cys Cys Gly Ala Gly Gly Ala Cys Ala Cys
            260                 265                 270

Gly Gly Cys Cys Gly Thr Gly Thr Ala Thr Thr Ala Cys Thr Gly Thr
            275                 280                 285

Gly Cys Gly Ala Gly Ala Gly Gly Thr Cys Gly Gly Ala Cys Thr Gly
            290                 295                 300

Ala Gly Gly Thr Gly Gly Cys Ala Ala Cys Cys Cys Cys Gly Gly
305                 310                 315                 320

Cys Gly Cys Cys Thr Ala Cys Thr Gly Gly Gly Gly Cys Cys Ala Ala
                325                 330                 335

Gly Gly Gly Ala Cys Ala Ala Thr Gly Gly Thr Cys Ala Cys Cys Gly
            340                 345                 350

Thr Cys Thr Cys Gly Ala Gly Thr
            355                 360

<210> SEQ ID NO 2
<211> LENGTH: 120
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Thr Glu Val Ala Thr Pro Gly Ala Tyr Trp Gly Gln
            100                 105                 110

Gly Thr Met Val Thr Val Ser Ser
        115                 120

<210> SEQ ID NO 3
<211> LENGTH: 333
<212> TYPE: DNA
<213> ORGANISM: Homo sapiens

<400> SEQUENCE: 3
caggctgtgc tgactcagcc gtcctcagtg tctggggccc cagggcagag ggtcaccatc      60
tcctgcactg ggagcagctc aacatcggg gcaggttatg atgtacactg gtaccagcag     120
cttccaggaa cagcccccaa actcctcatc tatggtaaca gcaatcggcc ctcagggtc     180 cctgaccgat tctctggctc caagtctggc acctcagcct ccctggccgt cactgggctc     240
caggctgagg atgaggctga ttattactgc agtcctatg acagcagcct gagtgatgtg     300
gtattcggcg agggaccaa gctgaccgtc cta                                  333

<210> SEQ ID NO 4
<211> LENGTH: 111
<212> TYPE: PRT
<213> ORGANISM: Homo sapiens

<400> SEQUENCE: 4

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Val Thr Gly Leu
65                  70                  75                  80

Gln Ala Glu Asp Glu Ala Asp Tyr Tyr Cys Gln Ser Tyr Asp Ser Ser
                85                  90                  95

Leu Ser Asp Val Val Phe Gly Gly Gly Thr Lys Leu Thr Val Leu
            100                 105                 110

<210> SEQ ID NO 5
<211> LENGTH: 366
<212> TYPE: DNA
<213> ORGANISM: Homo sapiens

<400> SEQUENCE: 5
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc gagatatcgg     300

```
gactatggtg gtaactccca cctctttgac tactgggggc aagggaccac ggtcaccgtc    360
tcgagt                                                               366
```

<210> SEQ ID NO 6
<211> LENGTH: 122
<212> TYPE: PRT
<213> ORGANISM: Homo sapiens

<400> SEQUENCE: 6

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Asp Tyr Gly Asn Ser His Leu Phe Asp Tyr Trp
            100                 105                 110

Gly Gln Gly Thr Thr Val Thr Val Ser Ser
        115                 120
```

<210> SEQ ID NO 7
<211> LENGTH: 321
<212> TYPE: DNA
<213> ORGANISM: Homo sapiens

<400> SEQUENCE: 7

```
gaaattgtga tgacgcagtc tccgtcctcc ctgcctgcct ctgtaggaga cagagtcacc     60
atcacttgtc gggcaagtca gaacattaag acctatttgc actggtacca acagaagcca   120
gggaaagccc ctaacctcct gatctatgct gcatccaatt tgcaaattgg ggtcccatca   180
aggttcagtg gcagtggatc tgggacagat tttactctca ccatcagcag tctgcaacct   240
gaagattttg ctacttactt ctgtcaacag agttacatta cccctcccac cttcggccaa   300
gggacacgac tggagattaa a                                             321
```

<210> SEQ ID NO 8
<211> LENGTH: 107
<212> TYPE: PRT
<213> ORGANISM: Homo sapiens

<400> SEQUENCE: 8

```
Glu Ile Val Met Thr Gln Ser Pro Ser Ser Leu Pro Ala Ser Val Gly
 1               5                  10                  15

Asp Arg Val Thr Ile Thr Cys Arg Ala Ser Gln Asn Ile Lys Thr Tyr
            20                  25                  30

Leu His Trp Tyr Gln Gln Lys Pro Gly Lys Ala Pro Asn Leu Leu Ile
        35                  40                  45

Tyr Ala Ala Ser Asn Leu Gln Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Phe Cys Gln Gln Ser Tyr Ile Thr Pro Pro
                85                  90                  95
Thr Phe Gly Gln Gly Thr Arg Leu Glu Ile Lys
            100                 105
```

<210> SEQ ID NO 9
<211> LENGTH: 354
<212> TYPE: DNA
<213> ORGANISM: Homo sapiens

<400> SEQUENCE: 9

```
ggggtccagc tggtacagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccta gtggtggtag cacaagctac    180
gcacagaagt tccagggcag agtcaccatg accagggaca cgtccacgag cacagtctac   240
atggagctga gcagcctgag atctgaggac acggccgtat attactgtgc tagaaggggtt  300
atttcgggtg cttttgatat ctggggccag gggacaatgg tcaccgtctc gagt         354
```

<210> SEQ ID NO 10
<211> LENGTH: 118
<212> TYPE: PRT
<213> ORGANISM: Homo sapiens

<400> SEQUENCE: 10

```
Gly Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Arg Val Ile Ser Gly Ala Phe Asp Ile Trp Gly Gln Gly Thr
            100                 105                 110
Met Val Thr Val Ser Ser
        115
```

<210> SEQ ID NO 11
<211> LENGTH: 321
<212> TYPE: DNA
<213> ORGANISM: Homo sapiens

<400> SEQUENCE: 11

```
gacatccaga tgacccagtc tccttccacc ctgtctgcat ctattggaga cagagtcacc    60
atcacctgcc gggccagtga gggtatttat cactggttgg cctggtatca gcagaagcca   120
gggaaagccc ctaaactcct gatctataag gcctctagtt tagccagtgg ggccccatca   180
aggttcagcg gcagtgggtc tgggacagat ttcactctca ccatcagcag cctgcagcct   240
gatgattttg caacttatta ctgccaacaa tatagtaatt atccgctcac tttcggcgga   300
gggaccaagc tggagatcaa a                                             321
```

<210> SEQ ID NO 12
<211> LENGTH: 107
<212> TYPE: PRT
<213> ORGANISM: Homo sapiens

<400> SEQUENCE: 12

```
Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys
            100                 105
```

<210> SEQ ID NO 13
<211> LENGTH: 369
<212> TYPE: DNA
<213> ORGANISM: Homo sapiens

<400> SEQUENCE: 13

```
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacagg gcttgagtg gatggggata atcaacccta gtgatggtag cacaaggtac      180
gtagagaagt tccagggcag agtcaccatg accagggaca cgtccacgag cacagtctac     240
atggagttga gcagcctgag atctgaggac acggccgtgt atttctgtgc gagaggcatg     300
ggacccggcc cccactacca cttctacatg gacgtctggg gcaaagggac aatggtcacc     360
gtctcctca                                                             369
```

<210> SEQ ID NO 14
<211> LENGTH: 123
<212> TYPE: PRT
<213> ORGANISM: Homo sapiens

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asp Gly Ser Thr Arg Tyr Val Glu Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Gly Met Gly Pro Gly Pro His Tyr His Phe Tyr Met Asp Val
            100                 105                 110
```

```
Trp Gly Lys Gly Thr Met Val Thr Val Ser Ser
        115                 120
```

<210> SEQ ID NO 15
<211> LENGTH: 324
<212> TYPE: DNA
<213> ORGANISM: Homo sapiens

<400> SEQUENCE: 15

```
tcgtctgagc tgactcagga ccctgctgtg tctgtggcct tgggacagac agtcaggatc    60
acttgccaag agacagtct cagaagctat tacacaaact ggttccagca aaagccagga   120
caggcccctc tacttgtcgt ctatgctaaa aataagcggc cctcagggat cccagaccga   180
ttctctggct ccagctcggg aaacacagct tccttgacca tcactgggc tcaggcggaa   240 gatgaggctg actattactg tcattcccgg gacagcggtg gtaaccatgt gcttttcggc   300
ggagggacca agctgaccgt ccta                                         324
```

<210> SEQ ID NO 16
<211> LENGTH: 108
<212> TYPE: PRT
<213> ORGANISM: Homo sapiens

<400> SEQUENCE: 16

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Thr
            20                  25                  30

Asn Trp Phe Gln Gln Lys Pro Gly Gln Ala Pro Leu Leu Val Val Tyr
        35                  40                  45

Ala Lys Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys His Ser Arg Asp Ser Gly Gly Asn His
                85                  90                  95

Val Leu Phe Gly Gly Gly Thr Lys Leu Thr Val Leu
            100                 105
```

<210> SEQ ID NO 17
<211> LENGTH: 375
<212> TYPE: DNA
<213> ORGANISM: Homo sapiens

<400> SEQUENCE: 17

```
caggtgcagc tggtgcagtc tggggctgag gtgaagaagc ctggggcctc agtgaaggtc    60
tcctgcaagg cttctggtta cacctttacc ggccagtaca tccactgggt gcgacaggcc   120
cctggacaag gcttgagtg gatgggatgg atcagcgctt acaatggtta cacagactat   180
gcacagaagg tccagggcag agtcaccatg accacagaca catccaccag cacagcctac   240
atggagctga ggagcctgag atctgacgac acggccgtgt attactgtgc gagagaggtg   300
tggccagtgg cagcagctga tacattcagt gtttttgata tctggggccg aggaaccctg   360
gtcaccgtct cgagt                                                   375
```

<210> SEQ ID NO 18
<211> LENGTH: 125
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Gln
            20                  25                  30

Tyr Ile His Trp Val Arg Gln Ala Pro Gly Gln Gly Leu Glu Trp Met
        35                  40                  45

Gly Trp Ile Ser Ala Tyr Asn Gly Tyr Thr Asp Tyr Ala Gln Lys Val
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Val Trp Pro Val Ala Ala Ala Asp Thr Phe Ser Val Phe
            100                 105                 110

Asp Ile Trp Gly Arg Gly Thr Leu Val Thr Val Ser Ser
        115                 120                 125

<210> SEQ ID NO 19
<211> LENGTH: 324
<212> TYPE: DNA
<213> ORGANISM: Homo sapiens

<400> SEQUENCE: 19
tcgtctgagc tgactcagga ccctgctgtg tctgtggcct tgggacagac agtcaggatc      60
acatgccaag agacagcct cagaagctat tatgcaagct ggtaccagca gaagccagga     120 caggccctg tacttgtcat ctatggtaaa acaaccggc cctcagggat cccagaccga     180
ttctctggct ccagctcagg aaacacagct tccttgacca tcactggggc tcaggcggaa    240
gatgaggctg actattactg taactcccgg gacagcagtg gtaaccatgt ggtattcggc    300
ggagggacca agctgaccgt ccta                                            324

<210> SEQ ID NO 20
<211> LENGTH: 108
<212> TYPE: PRT
<213> ORGANISM: Homo sapiens

<400> SEQUENCE: 20

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 21
<211> LENGTH: 354

```
<212> TYPE: DNA
<213> ORGANISM: Homo sapiens

<400> SEQUENCE: 21
gaggtgcagc tgttggagtc tggggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagatggg    300
accacggggt tgcatgactc ctggggccaa gggacaatgg tcaccgtctc gagt          354

<210> SEQ ID NO 22
<211> LENGTH: 118
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Thr Gly Leu His Asp Ser Trp Gly Gln Gly Thr
            100                 105                 110

Met Val Thr Val Ser Ser
        115

<210> SEQ ID NO 23
<211> LENGTH: 333
<212> TYPE: DNA
<213> ORGANISM: Homo sapiens

<400> SEQUENCE: 23
cagtctgtgt tgacgcagcc gccctcagcg tctgggaccc ccggacagag ggtcactatc      60
tcttgttctg gaagcagttc caacgtcgga agtaattttg tatattggta ccagcagttc    120
ccaggaacgg ccccccaaact cctcatctat aggaataatc agcggccctc aggggtccct    180
gaccgattct ctggctccaa gtccggcacc tcagcctccc tggccattag tggcctccgg    240
tccgaggatg aggctgatta ttactgtgca gcatgggatg acaccctgaa tggtcactac    300
gtgttcggcg agggaccaa gctgaccgtc cta                                    333

<210> SEQ ID NO 24
<211> LENGTH: 111
<212> TYPE: PRT
<213> ORGANISM: Homo sapiens

<400> SEQUENCE: 24

Gln Ser Val Leu Thr Gln Pro Pro Ser Ala Ser Gly Thr Pro Gly Gln
1               5                   10                  15
```

Arg Val Thr Ile Ser Cys Ser Gly Ser Ser Asn Val Gly Ser Asn
            20                  25                  30

Phe Val Tyr Trp Tyr Gln Gln Phe Pro Gly Thr Ala Pro Lys Leu Leu
         35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Thr Leu
                 85                  90                  95

Asn Gly His Tyr Val Phe Gly Gly Gly Thr Lys Leu Thr Val Leu
            100                 105                 110

<210> SEQ ID NO 25
<211> LENGTH: 354
<212> TYPE: DNA
<213> ORGANISM: Homo sapiens

<400> SEQUENCE: 25
gaggtccagc tggtgcagtc tggagcagag gtgaaaaagc ccggggagtc tctgaagatc      60
tcctgtaagg gatatggata cgatttcagt cgcgactgga tcgcctgggt gcgccagatg     120
cccgggaaag gcctggagtg gatggggatc atctatcctg gtgactctga taccagatac     180
agcccgtcct tcgaaggcca ggtcaccatc tcagccgaca agtccatcag caccgcctac     240
ctgcagtgga aagcctgaa ggcctcggac accgccatgt attactgtgc gagacaacgg     300
aggttggggt ggttcgaccc ctggggccag gggacaatgg tcaccgtctc ttca           354

<210> SEQ ID NO 26
<211> LENGTH: 118
<212> TYPE: PRT
<213> ORGANISM: Homo sapiens

<400> SEQUENCE: 26

Glu Val Gln Leu Val Gln Ser Gly Ala Glu Val Lys Lys Pro Gly Glu
1               5                  10                  15

Ser Leu Lys Ile Ser Cys Lys Gly Tyr Gly Tyr Asp Phe Ser Arg Asp
            20                  25                  30

Trp Ile Ala Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                  55                  60

Glu Gly Gln Val Thr Ile Ser Ala Asp Lys Ser Ile Ser Thr Ala Tyr
 65                  70                  75                  80

Leu Gln Trp Arg Ser Leu Lys Ala Ser Asp Thr Ala Met Tyr Tyr Cys
                 85                  90                  95

Ala Arg Gln Arg Arg Leu Gly Trp Phe Asp Pro Trp Gly Gln Gly Thr
            100                 105                 110

Met Val Thr Val Ser Ser
        115

<210> SEQ ID NO 27
<211> LENGTH: 330
<212> TYPE: DNA
<213> ORGANISM: Homo sapiens

<400> SEQUENCE: 27
cggtctgtgt tgacgcagcc gccctcagtg tctgcggccc caggacagaa ggtcaccatt      60

```
tcctgctctg gaagcacctc aacattggg aataattatg tctcctggta ccaacagcac    120
ccaggcaaag ccccaaact catgatttat gatgtcagta agcggccctc aggggtccct    180
gaccgattct ctggctccaa gtctggcaac tcagcctccc tggacatcag tgggctccag    240
tctgaggatg aggctgatta ttactgtgca gcatgggatg acagcctgag tgaatttctc    300
ttcggaactg ggaccaagct gaccgtccta                                    330
```

<210> SEQ ID NO 28
<211> LENGTH: 110
<212> TYPE: PRT
<213> ORGANISM: Homo sapiens

<400> SEQUENCE: 28

Arg Ser Val Leu Thr Gln Pro Pro Ser Val Ala Ala Pro Gly Gln
1               5                   10                  15

Lys Val Thr Ile Ser Cys Ser Gly Ser Thr Ser Asn Ile Gly Asn Asn
            20                  25                  30

Tyr Val Ser Trp Tyr Gln Gln His Pro Gly Lys Ala Pro Lys Leu Met
        35                  40                  45

Ile Tyr Asp Val Ser Lys Arg Pro Ser Gly Val Pro Asp Arg Phe Ser
    50                  55                  60

Gly Ser Lys Ser Gly Asn Ser Ala Ser Leu Asp Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Glu Phe Leu Phe Gly Thr Gly Thr Lys Leu Thr Val Leu
            100                 105                 110

<210> SEQ ID NO 29
<211> LENGTH: 369
<212> TYPE: DNA
<213> ORGANISM: Homo sapiens

<400> SEQUENCE: 29

```
gaggtgcagc tgttggagtc tgggggaggc ttggtacagc ctgggggtc cctgagactc     60 tcctgtgcag cctctggatt caccttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagacattta    300
ccgtctgggt ctagcagcag ttgggccttt gactcctggg gcgagggac cacggtcacc    360 gtctcgagt                                                           369
```

<210> SEQ ID NO 30
<211> LENGTH: 123
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Leu Pro Ser Gly Ser Ser Ser Trp Ala Phe Asp Ser
            100                 105                 110

Trp Gly Arg Gly Thr Thr Val Thr Val Ser Ser
            115                 120
```

<210> SEQ ID NO 31
<211> LENGTH: 330
<212> TYPE: DNA
<213> ORGANISM: Homo sapiens

<400> SEQUENCE: 31

```
tcctatgtgc tgactcagcc accctcagcg tctgggaccc ccgggcagag ggtcaccatc     60
tcttgttctg gaagcagctc caacatcgga agtaattatg tatactggta ccagcagctc    120
ccaggaacgg ccccccaaact cctcatctat aggaataatc agcggccctc aggggtccct   180
gaccgattct ctggctccaa gtctggcacc tcagcctccc tggccatcag tgggctccag   240
tctgaggatg aggctgatta ttactgtgag catgggatga caacgtcga tggtccggtg    300 ttcggcgggg ggaccaagct gaccgtccta                                     330
```

<210> SEQ ID NO 32
<211> LENGTH: 110
<212> TYPE: PRT
<213> ORGANISM: Homo sapiens

<400> SEQUENCE: 32

```
Ser Tyr Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
         35                  40                  45

Ile Tyr Arg Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Glu Ala Trp Asp Asp Asn Val
                 85                  90                  95

Asp Gly Pro Val Phe Gly Gly Gly Thr Lys Leu Thr Val Leu
            100                 105                 110
```

<210> SEQ ID NO 33
<211> LENGTH: 1337
<212> TYPE: PRT
<213> ORGANISM: Homo sapiens

<400> SEQUENCE: 33

```
Met Lys Pro Ala Ala Arg Glu Ala Arg Leu Pro Pro Arg Ser Pro Gly
 1               5                  10                  15

Leu Arg Trp Ala Leu Pro Leu Leu Leu Leu Leu Arg Leu Gly Gln
            20                  25                  30
```

-continued

```
Ile Leu Cys Ala Gly Gly Thr Pro Ser Pro Ile Pro Asp Pro Ser Val
         35                  40                  45

Ala Thr Val Ala Thr Gly Glu Asn Gly Ile Thr Gln Ile Ser Ser Thr
 50                  55                  60

Ala Glu Ser Phe His Lys Gln Asn Gly Thr Gly Thr Pro Gln Val Glu
 65                  70                  75                  80

Thr Asn Thr Ser Glu Asp Gly Glu Ser Ser Gly Ala Asn Asp Ser Leu
                 85                  90                  95

Arg Thr Pro Glu Gln Gly Ser Asn Gly Thr Asp Gly Ala Ser Gln Lys
            100                 105                 110

Thr Pro Ser Ser Thr Gly Pro Ser Pro Val Phe Asp Ile Lys Ala Val
            115                 120                 125

Ser Ile Ser Pro Thr Asn Val Ile Leu Thr Trp Lys Ser Asn Asp Thr
130                 135                 140

Ala Ala Ser Glu Tyr Lys Tyr Val Val Lys His Lys Met Glu Asn Glu
145                 150                 155                 160

Lys Thr Ile Thr Val Val His Gln Pro Trp Cys Asn Ile Thr Gly Leu
                165                 170                 175

Arg Pro Ala Thr Ser Tyr Val Phe Ser Ile Thr Pro Gly Ile Gly Asn
            180                 185                 190

Glu Thr Trp Gly Asp Pro Arg Val Ile Lys Val Ile Thr Glu Pro Ile
            195                 200                 205

Pro Val Ser Asp Leu Arg Val Ala Leu Thr Gly Val Arg Lys Ala Ala
            210                 215                 220

Leu Ser Trp Ser Asn Gly Asn Gly Thr Ala Ser Cys Arg Val Leu Leu
225                 230                 235                 240

Glu Ser Ile Gly Ser His Glu Glu Leu Thr Gln Asp Ser Arg Leu Gln
                245                 250                 255

Val Asn Ile Ser Asp Leu Lys Pro Gly Val Gln Tyr Asn Ile Asn Pro
            260                 265                 270

Tyr Leu Leu Gln Ser Asn Lys Thr Lys Gly Asp Pro Leu Gly Thr Glu
            275                 280                 285

Gly Gly Leu Asp Ala Ser Asn Thr Glu Arg Ser Arg Ala Gly Ser Pro
290                 295                 300

Thr Ala Pro Val His Asp Glu Ser Leu Val Gly Pro Val Asp Pro Ser
305                 310                 315                 320

Ser Gly Gln Gln Ser Arg Asp Thr Glu Val Leu Leu Val Gly Leu Glu
                325                 330                 335

Pro Gly Thr Arg Tyr Asn Ala Thr Val Tyr Ser Gln Ala Ala Asn Gly
            340                 345                 350

Thr Glu Gly Gln Pro Gln Ala Ile Glu Phe Arg Thr Asn Ala Ile Gln
            355                 360                 365

Val Phe Asp Val Thr Ala Val Asn Ile Ser Ala Thr Ser Leu Thr Leu
            370                 375                 380

Ile Trp Lys Val Ser Asp Asn Glu Ser Ser Ser Asn Tyr Thr Tyr Lys
385                 390                 395                 400

Ile His Val Ala Gly Glu Thr Asp Ser Ser Asn Leu Asn Val Ser Glu
                405                 410                 415

Pro Arg Ala Val Ile Pro Gly Leu Arg Ser Ser Thr Phe Tyr Asn Ile
            420                 425                 430

Thr Val Cys Pro Val Leu Gly Asp Ile Glu Gly Thr Pro Gly Phe Leu
            435                 440                 445
```

-continued

```
Gln Val His Thr Pro Val Pro Val Ser Asp Phe Arg Val Thr Val
    450                 455                 460
Val Ser Thr Thr Glu Ile Gly Leu Ala Trp Ser Ser His Asp Ala Glu
465                 470                 475                 480
Ser Phe Gln Met His Ile Thr Gln Glu Gly Ala Gly Asn Ser Arg Val
                485                 490                 495
Glu Ile Thr Thr Asn Gln Ser Ile Ile Ile Gly Gly Leu Phe Pro Gly
                500                 505                 510
Thr Lys Tyr Cys Phe Glu Ile Val Pro Lys Gly Pro Asn Gly Thr Glu
            515                 520                 525
Gly Ala Ser Arg Thr Val Cys Asn Arg Thr Val Pro Ser Ala Val Phe
        530                 535                 540
Asp Ile His Val Val Tyr Val Thr Thr Thr Glu Met Trp Leu Asp Trp
545                 550                 555                 560
Lys Ser Pro Asp Gly Ala Ser Glu Tyr Val Tyr His Leu Val Ile Glu
                565                 570                 575
Ser Lys His Gly Ser Asn His Thr Ser Thr Tyr Asp Lys Ala Ile Thr
                580                 585                 590
Leu Gln Gly Leu Ile Pro Gly Thr Leu Tyr Asn Ile Thr Ile Ser Pro
            595                 600                 605
Glu Val Asp His Val Trp Gly Asp Pro Asn Ser Thr Ala Gln Tyr Thr
        610                 615                 620
Arg Pro Ser Asn Val Ser Asn Ile Asp Val Ser Thr Asn Thr Thr Ala
625                 630                 635                 640
Ala Thr Leu Ser Trp Gln Asn Phe Asp Asp Ala Ser Pro Thr Tyr Ser
                645                 650                 655
Tyr Cys Leu Leu Ile Glu Lys Ala Gly Asn Ser Ser Asn Ala Thr Gln
            660                 665                 670
Val Val Thr Asp Ile Gly Ile Thr Asp Ala Thr Val Thr Glu Leu Ile
        675                 680                 685
Pro Gly Ser Ser Tyr Thr Val Glu Ile Phe Ala Gln Val Gly Asp Gly
    690                 695                 700
Ile Lys Ser Leu Glu Pro Gly Arg Lys Ser Phe Cys Thr Asp Pro Ala
705                 710                 715                 720
Ser Met Ala Ser Phe Asp Cys Glu Val Val Pro Lys Glu Pro Ala Leu
                725                 730                 735
Val Leu Lys Trp Thr Cys Pro Pro Gly Ala Asn Ala Gly Phe Glu Leu
            740                 745                 750
Glu Val Ser Ser Gly Ala Trp Asn Asn Ala Thr His Leu Glu Ser Cys
        755                 760                 765
Ser Ser Glu Asn Gly Thr Glu Tyr Arg Thr Glu Val Thr Tyr Leu Asn
    770                 775                 780
Phe Ser Thr Ser Tyr Asn Ile Ser Ile Thr Thr Val Ser Cys Gly Lys
785                 790                 795                 800
Met Ala Ala Pro Thr Arg Asn Thr Cys Thr Thr Gly Ile Thr Asp Pro
                805                 810                 815
Pro Pro Pro Asp Gly Ser Pro Asn Ile Thr Ser Val Ser His Asn Ser
                820                 825                 830
Val Lys Val Lys Phe Ser Gly Phe Glu Ala Ser His Gly Pro Ile Lys
        835                 840                 845
Ala Tyr Ala Val Ile Leu Thr Thr Gly Glu Ala Gly His Pro Ser Ala
    850                 855                 860
```

```
Asp Val Leu Lys Tyr Thr Tyr Asp Asp Phe Lys Lys Gly Ala Ser Asp
865                 870                 875                 880

Thr Tyr Val Thr Tyr Leu Ile Arg Thr Glu Glu Lys Gly Arg Ser Gln
                885                 890                 895

Ser Leu Ser Glu Val Leu Lys Tyr Glu Ile Asp Val Gly Asn Glu Ser
        900                 905                 910

Thr Thr Leu Gly Tyr Tyr Asn Gly Lys Leu Glu Pro Leu Gly Ser Tyr
            915                 920                 925

Arg Ala Cys Val Ala Gly Phe Thr Asn Ile Thr Phe His Pro Gln Asn
930                 935                 940

Lys Gly Leu Ile Asp Gly Ala Glu Ser Tyr Val Ser Phe Ser Arg Tyr
945                 950                 955                 960

Ser Asp Ala Val Ser Leu Pro Gln Asp Pro Gly Val Ile Cys Gly Ala
                965                 970                 975

Val Phe Gly Cys Ile Phe Gly Ala Leu Val Ile Val Thr Val Gly Gly
            980                 985                 990

Phe Ile Phe Trp Arg Lys Lys Arg  Lys Asp Ala Lys Asn  Asn Glu Val
        995                 1000                1005

Ser Phe  Ser Gln Ile Lys Pro  Lys Lys Ser Lys Leu  Ile Arg Val
1010                1015                1020

Glu Asn  Phe Glu Ala Tyr  Phe Lys Lys Gln Gln Ala  Asp Ser Asn
1025                1030                1035

Cys Gly  Phe Ala Glu Glu  Tyr Glu Asp Leu Lys Leu  Val Gly Ile
1040                1045                1050

Ser Gln  Pro Lys Tyr Ala  Ala Glu Leu Ala Glu Asn  Arg Gly Lys
1055                1060                1065

Asn Arg  Tyr Asn Asn Val Leu  Pro Tyr Asp Ile Ser  Arg Val Lys
1070                1075                1080

Leu Ser  Val Gln Thr His Ser  Thr Asp Asp Tyr Ile  Asn Ala Asn
1085                1090                1095

Tyr Met  Pro Gly Tyr His Ser  Lys Lys Asp Phe Ile  Ala Thr Gln
1100                1105                1110

Gly Pro  Leu Pro Asn Thr Leu  Lys Asp Phe Trp Arg  Met Val Trp
1115                1120                1125

Glu Lys  Asn Val Tyr Ala Ile  Ile Met Leu Thr Lys  Cys Val Glu
1130                1135                1140

Gln Gly  Arg Thr Lys Cys Glu  Glu Tyr Trp Pro Ser  Lys Gln Ala
1145                1150                1155

Gln Asp  Tyr Gly Asp Ile Thr  Val Ala Met Thr Ser  Glu Ile Val
1160                1165                1170

Leu Pro  Glu Trp Thr Ile Arg  Asp Phe Thr Val Lys  Asn Ile Gln
1175                1180                1185

Thr Ser  Glu Ser His Pro Leu  Arg Gln Phe His Phe  Thr Ser Trp
1190                1195                1200

Pro Asp  His Gly Val Pro Asp  Thr Thr Asp Leu Leu  Ile Asn Phe
1205                1210                1215

Arg Tyr  Leu Val Arg Asp Tyr  Met Lys Gln Ser Pro  Pro Glu Ser
1220                1225                1230

Pro Ile  Leu Val His Cys Ser  Ala Gly Val Gly Arg  Thr Gly Thr
1235                1240                1245

Phe Ile  Ala Ile Asp Arg Leu  Ile Tyr Gln Ile Glu  Asn Glu Asn
1250                1255                1260
```

-continued

```
Thr Val Asp Val Tyr Gly Ile Val Tyr Asp Leu Arg Met His Arg
    1265            1270            1275

Pro Leu Met Val Gln Thr Glu Asp Gln Tyr Val Phe Leu Asn Gln
    1280            1285            1290

Cys Val Leu Asp Ile Val Arg Ser Gln Lys Asp Ser Lys Val Asp
    1295            1300            1305

Leu Ile Tyr Gln Asn Thr Thr Ala Met Thr Ile Tyr Glu Asn Leu
    1310            1315            1320

Ala Pro Val Thr Thr Phe Gly Lys Thr Asn Gly Tyr Ile Ala
    1325            1330            1335
```